US009233109B2

(12) United States Patent
Papke et al.

(10) Patent No.: US 9,233,109 B2
(45) Date of Patent: Jan. 12, 2016

(54) COMPOSITIONS, METHODS OF USE, AND METHODS OF TREATMENT

(75) Inventors: Roger Lee Papke, Gainesville, FL (US); Adriaan Willem Bruijnzeel, Gainesville, FL (US); Sara Jo Nixon, Gainesville, FL (US); William Kem, Gainesville, FL (US); Ferenc Soti, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 52 days.

(21) Appl. No.: 13/642,907

(22) PCT Filed: Apr. 22, 2011

(86) PCT No.: PCT/US2011/033574
§ 371 (c)(1),
(2), (4) Date: Nov. 9, 2012

(87) PCT Pub. No.: WO2011/133858
PCT Pub. Date: Oct. 27, 2011

(65) Prior Publication Data
US 2013/0137697 A1 May 30, 2013

Related U.S. Application Data

(60) Provisional application No. 61/327,321, filed on Apr. 23, 2010.

(51) Int. Cl.
*A61K 31/444* (2006.01)
*A61K 31/44* (2006.01)
*A61K 31/4995* (2006.01)
*A61K 45/06* (2006.01)
*A61K 31/445* (2006.01)

(52) U.S. Cl.
CPC ............. *A61K 31/4995* (2013.01); *A61K 31/44* (2013.01); *A61K 31/444* (2013.01); *A61K 31/445* (2013.01); *A61K 45/06* (2013.01)

(58) Field of Classification Search
CPC ... A61K 31/444; A61K 31/44; A61K 31/445; A61K 31/4995; A61K 45/06
See application file for complete search history.

(56) References Cited

U.S. PATENT DOCUMENTS

2005/0215571 A1  9/2005  Romano
2006/0128676 A1  6/2006  Shafer et al.
2006/0167039 A1  7/2006  Nguyen et al.
2006/0211686 A1  9/2006  Kohlhaas et al.
2009/0221648 A1  9/2009  Rueter et al.

OTHER PUBLICATIONS

International Search Report and Written Opinion dated Feb. 8, 2012.
Nides, et al., "Smoking Cessation with Varenicline, a Selective A4B2 Nicotinic Receptor Partial Agonist: Results from a 7-week, Randomized, Placebo-and Buprion-Controlled Trial with a 1-year Follow Up," Arch. Intern. Med., Aug. 2006, vol. 166, No. 15, pp. 1651-8156.
Olincy, et al., "Proof-of-Concept Trial of an Alpha7 Nicotinic Agonist in Schizophrenia," Arch. Gen. Psychiatry, 2006, vol. 63, No. 6, pp. 630-638.
Mineur, et al., "Cytisine-Based Nicotinic Partial Agonists as Novel Antidepressant Compounds," The Journal of Pharmacology and Experimental Therapeutics, vol. 329, No. 1, pp. 377-386, Apr. 1, 2009.
Horenstein, et al., "Multiple Pharmacophores for the Selective Activation of Nicotinic α7-Acetylcholine Receptors," Molecular Pharmacology, vol. 74, No. 6, 99. 1496-1511.
Bacher, et al., "Evidence for Nicotinic Receptor Modulation Specific to Neuropsychiatric Disorders: Therapeutic Implications," Primary Psychiatry. 2010;17(1):35-41.
Freedman, et al., "Initial Phase 2 Trial of a Nicotinic Agonist in Schizophrenia" Am J. Psychiatry, Aug. 2008, pp. 1040-1047.
Hashimoto, et al., "α7 Nicotinic Receptor Agonists as Potential Therapeutic Drugs for Schizophrenia," Curr. Med. Chem—Central Nervous System Agents, 2005, 5, 171-184.
Bacher, Ingrid et al. "Nicotinic receptor mechanisms in neuropsychiatric disorders: therapeutic implications." Primary Psychiatry 17.1 (2010): 35-41.
Smith, Robert C., et al. "Cognitive and antismoking effects of varenicline in patients with schizophrenia or schizoaffective disorder." Schizophrenia research 110.1 (2009): 149-155.
International Preliminary Report on Patentability dated Nov. 1, 2012.

*Primary Examiner* — Kara R McMillian
(74) *Attorney, Agent, or Firm* — Thomas | Horstemeyer, LLP

(57) ABSTRACT

Briefly described, embodiments of this disclosure, among others, include compositions, pharmaceutical compositions, methods of treating nicotine dependence, methods of treating a subject who smokes and has a risk for depression or other neuropsychiatric disorder, method of treating a subject who smokes and has a risk for depression or other neuropsychiatric disorders, and the like.

8 Claims, 20 Drawing Sheets

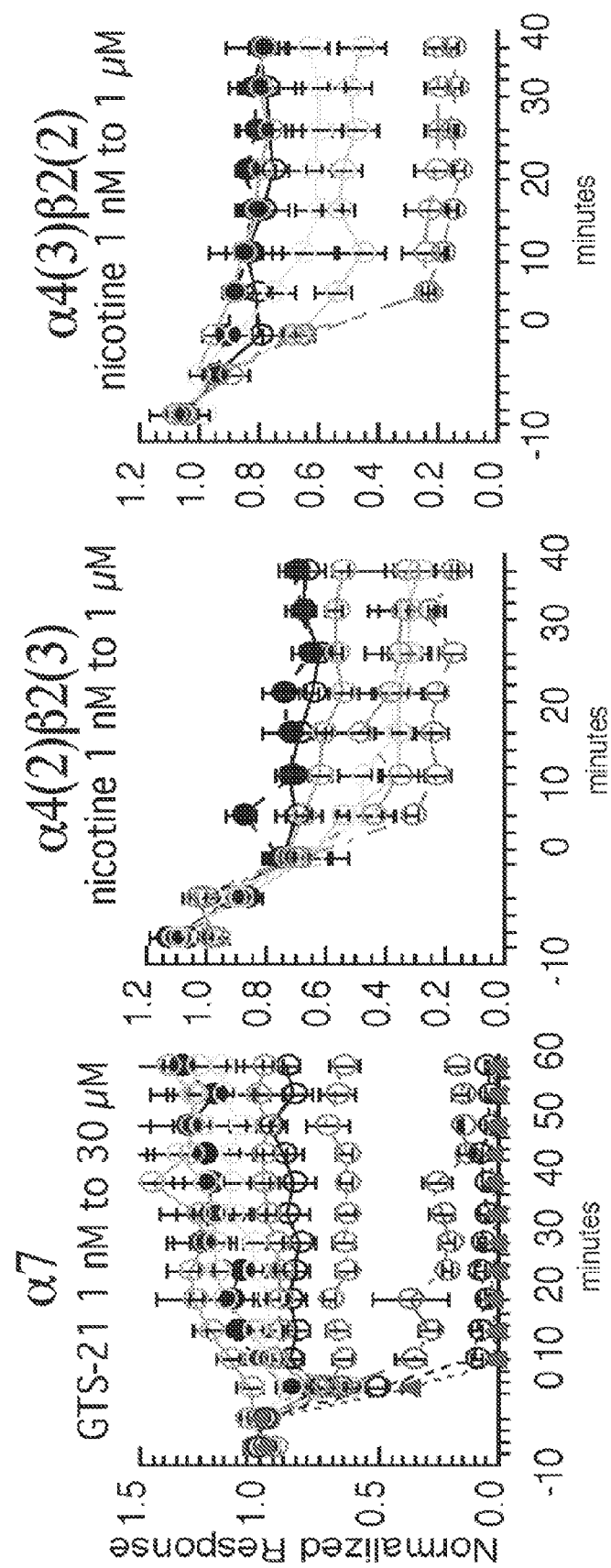
FIG. 1.1

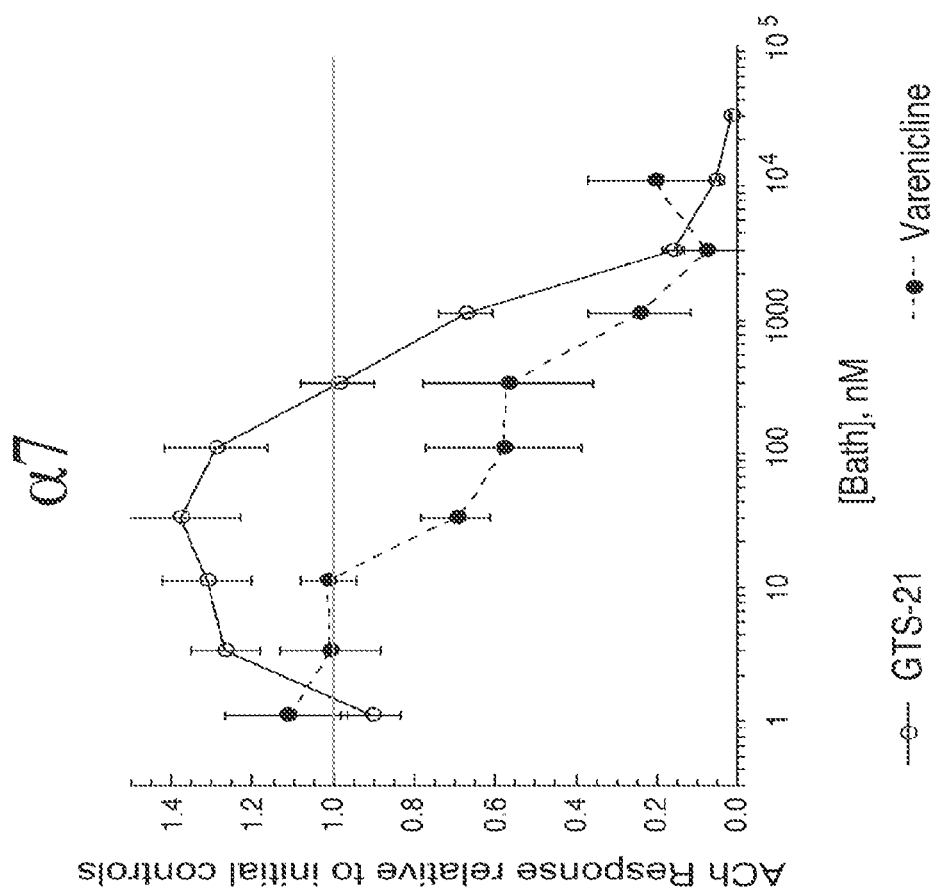
FIG. 1.2

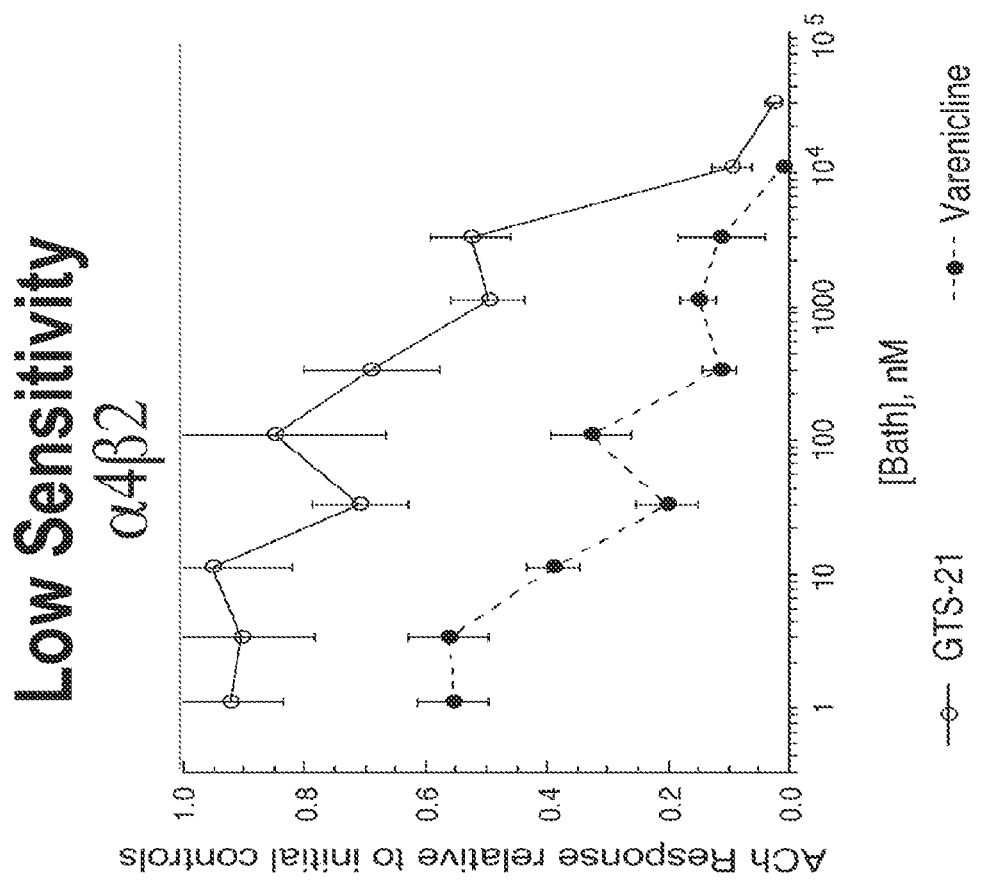
FIG. 1.2 (cont)

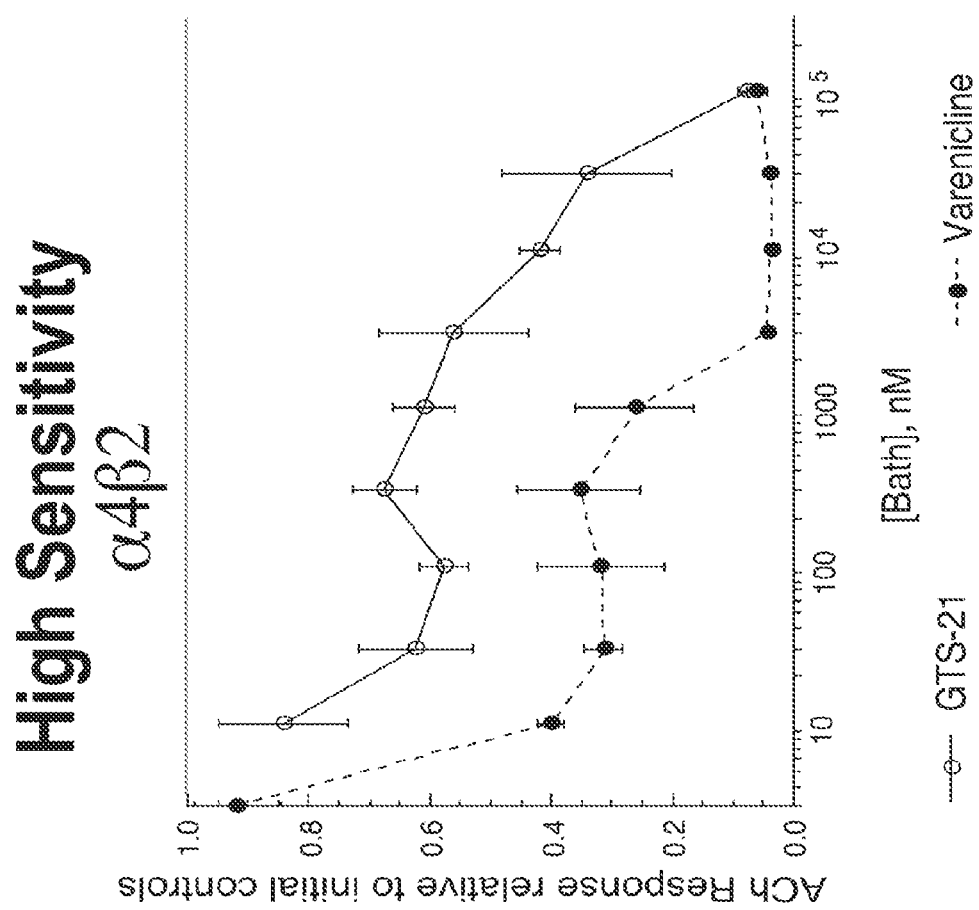
FIG. 1.2 (cont)

$$\text{Response} = \left(\frac{[a]}{[a+p]}\right) \cdot \left(\frac{\left(\frac{[a]^2}{[a+p]}\right)^{n_a}}{\left(\frac{[a]^2}{[a+p]}\right)^{n_a} + (EC_{50a})^{n_a}}\right) + \left(\frac{[p]}{[a+p]}\right) \cdot \left(\frac{R_{Max,p}\left(\frac{[p]^2}{[a+p]}\right)^{n_p}}{\left(\frac{[p]^2}{[a+p]}\right)^{n_p} + (EC_{50p})^{n_p}}\right) \times \left(1 - \frac{I_{Max,i}\,([pi])^{n_i}}{([pi])^{n_i} + (IC_{50p})^{n_i}}\right)$$

- Receptor availability factor
- Adjustment for effective concentration of full agonist
- Receptor availability factor
- Adjustment for effective concentration of partial agonist
- Noncompetitive inhibition factor

FIG. 2.1

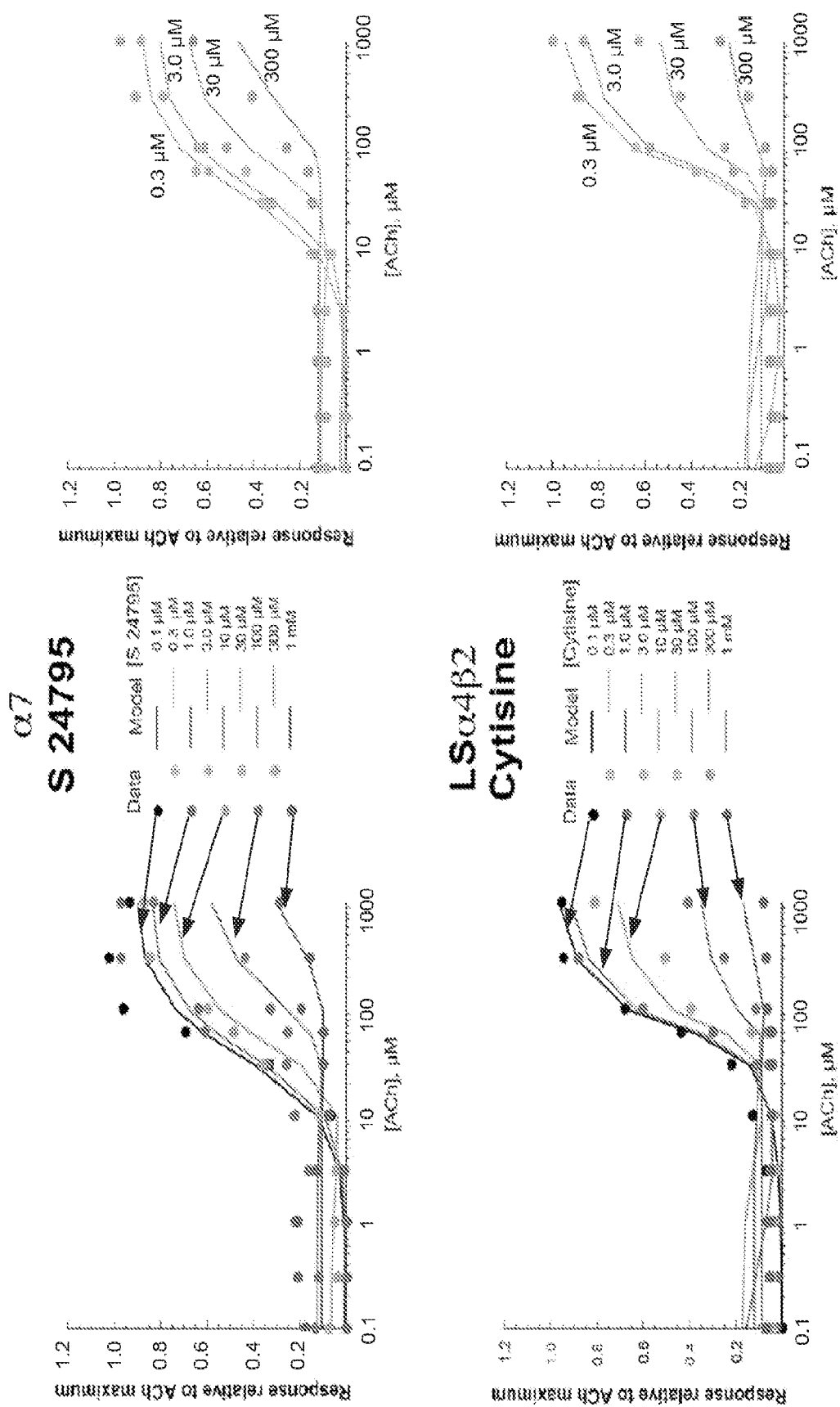
FIG. 2.2

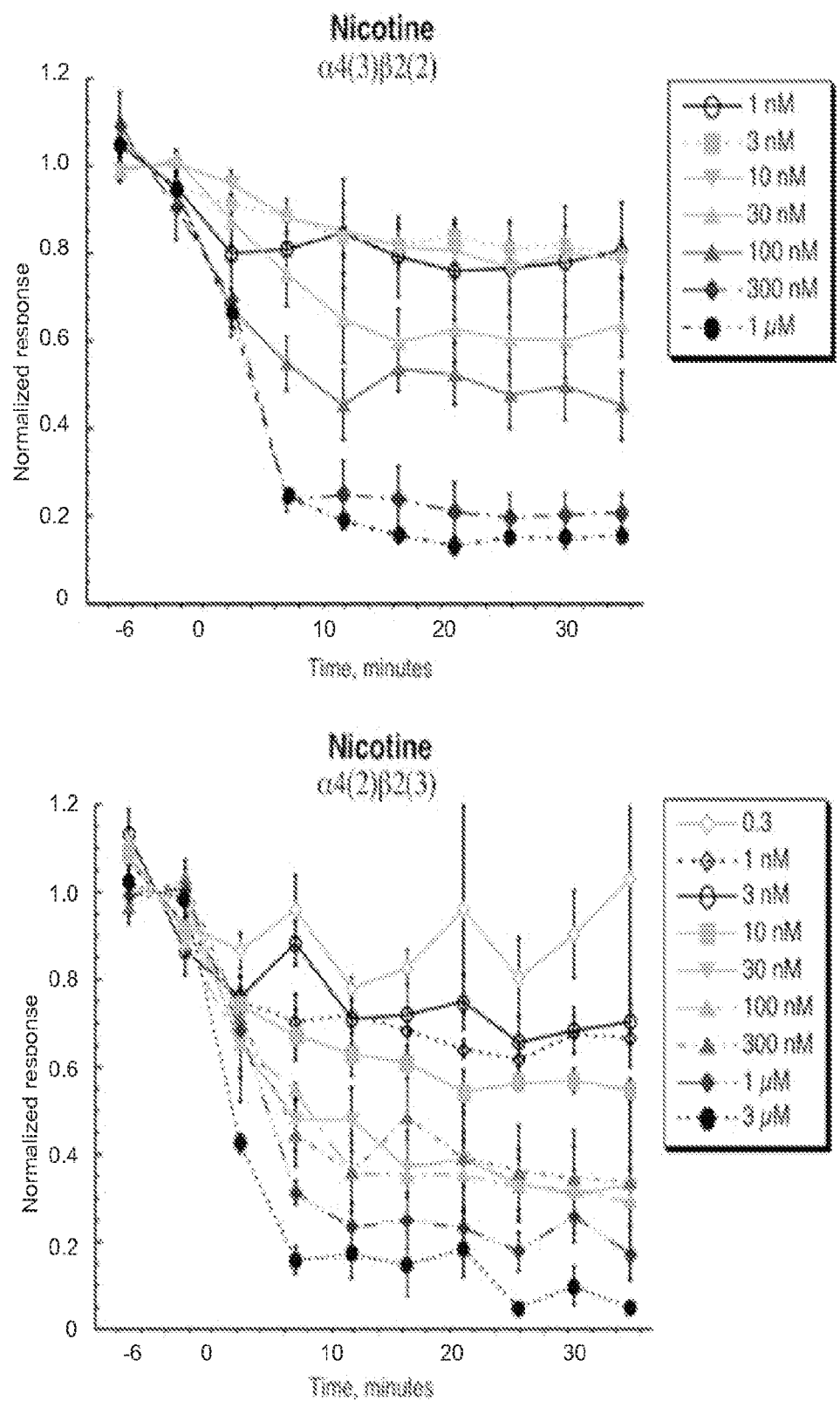
FIG. 2.3, part 1

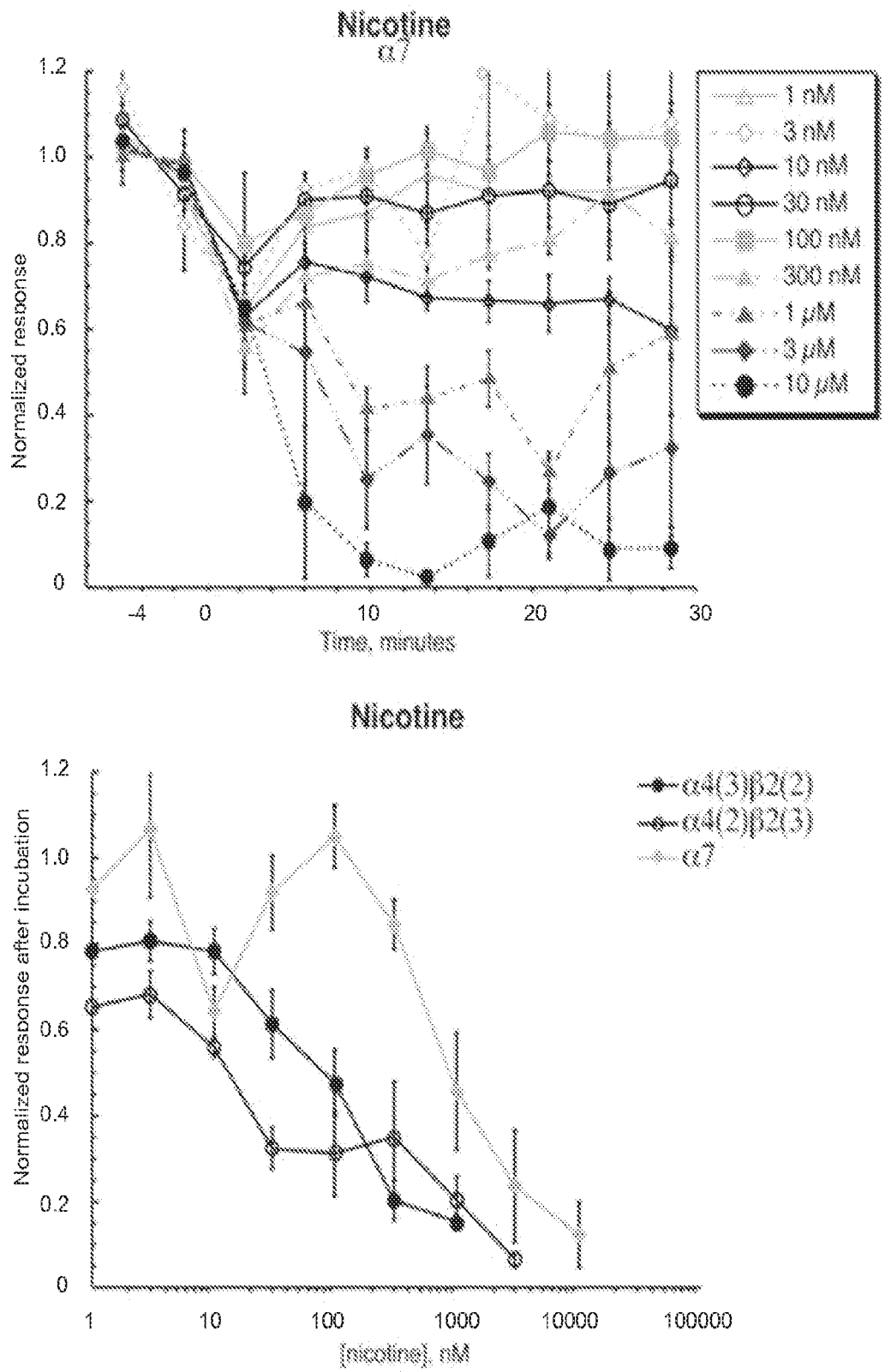
FIG. 2.3, part 2

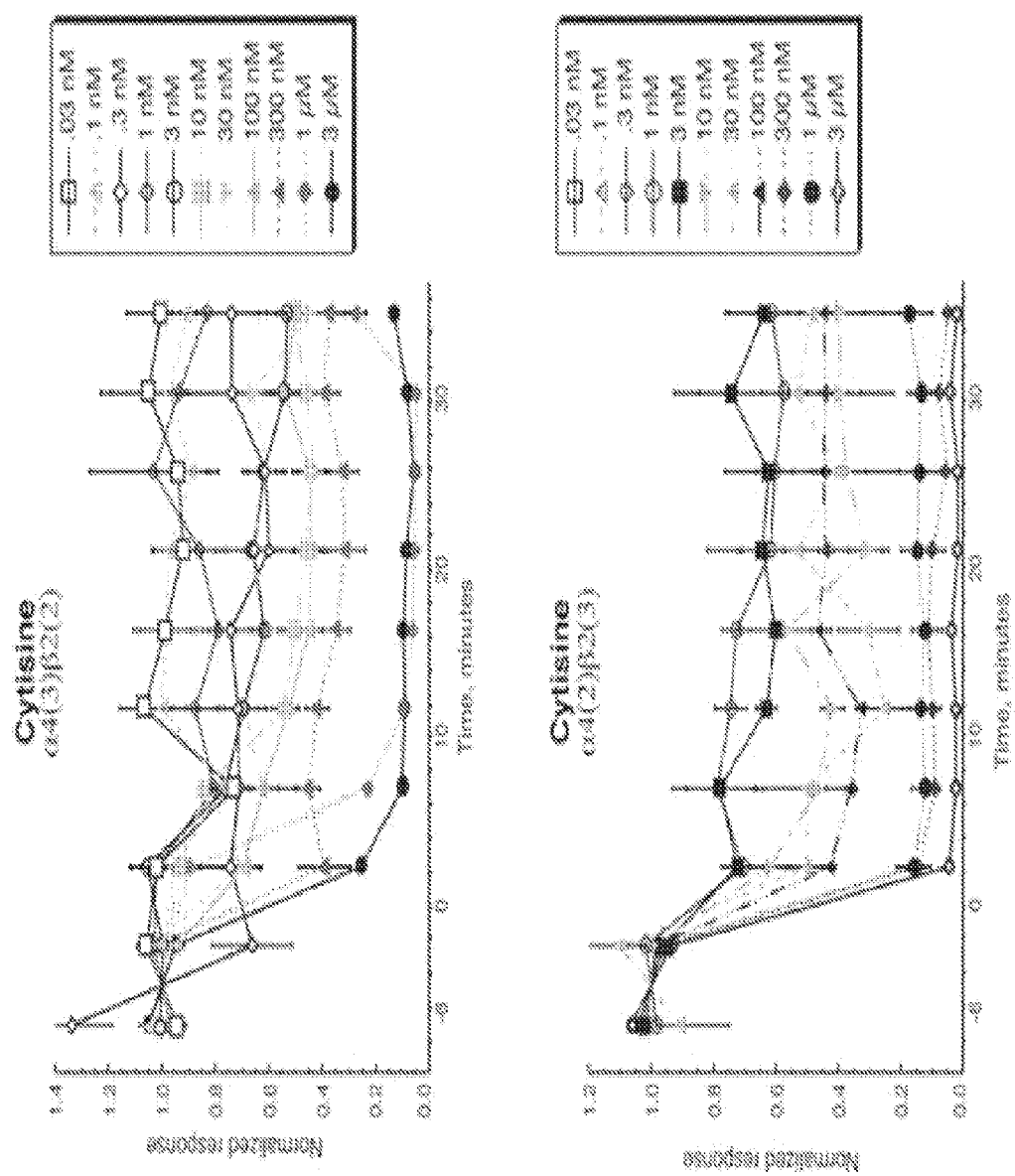
FIG. 2.4, part 1

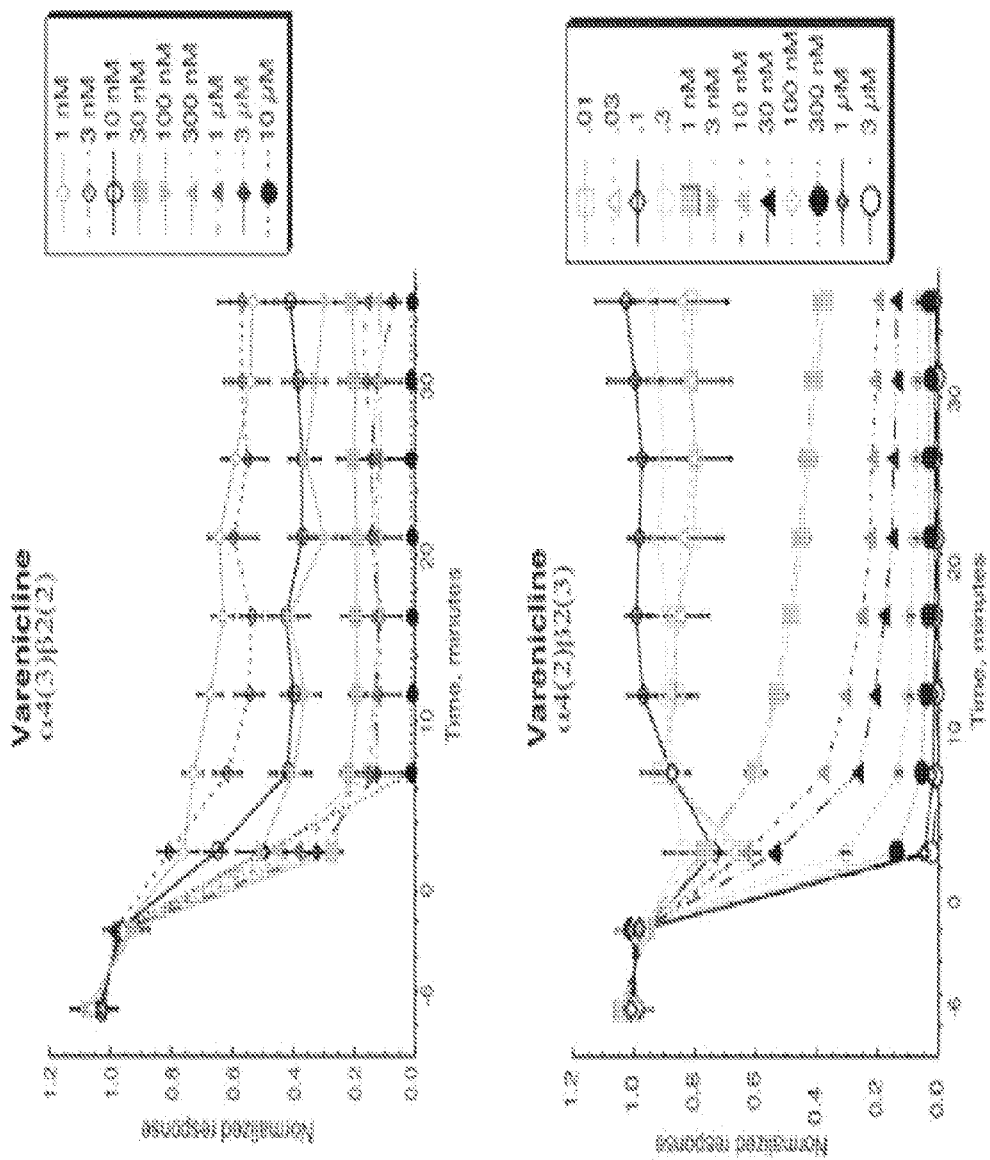
FIG. 2.4, part 2

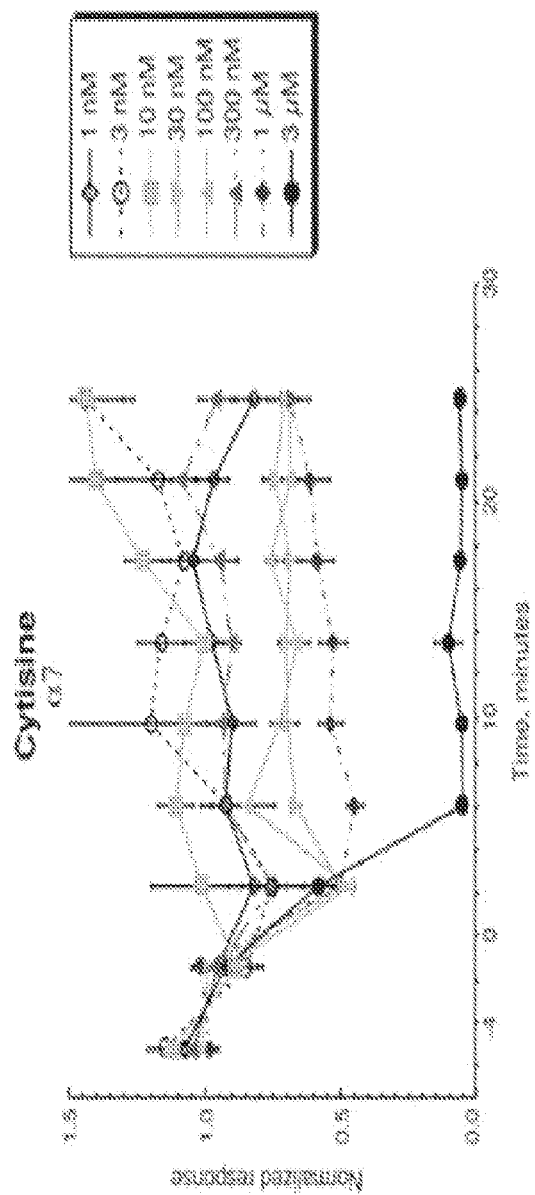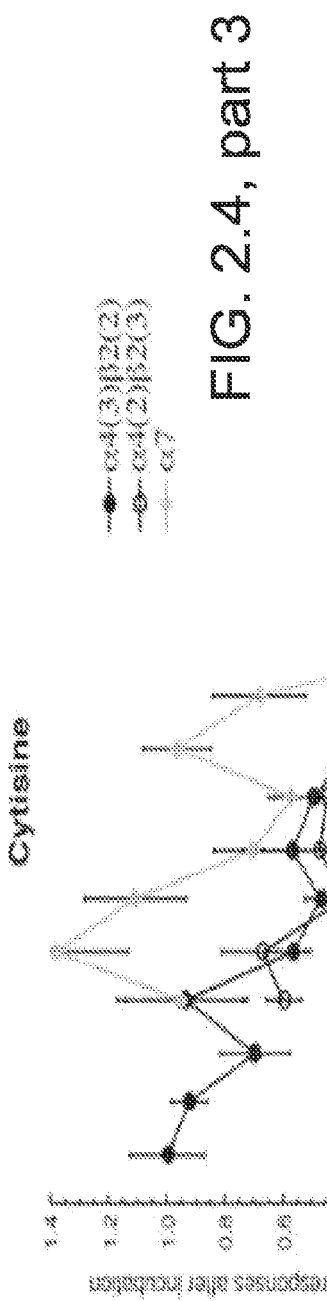
FIG. 2.4, part 3

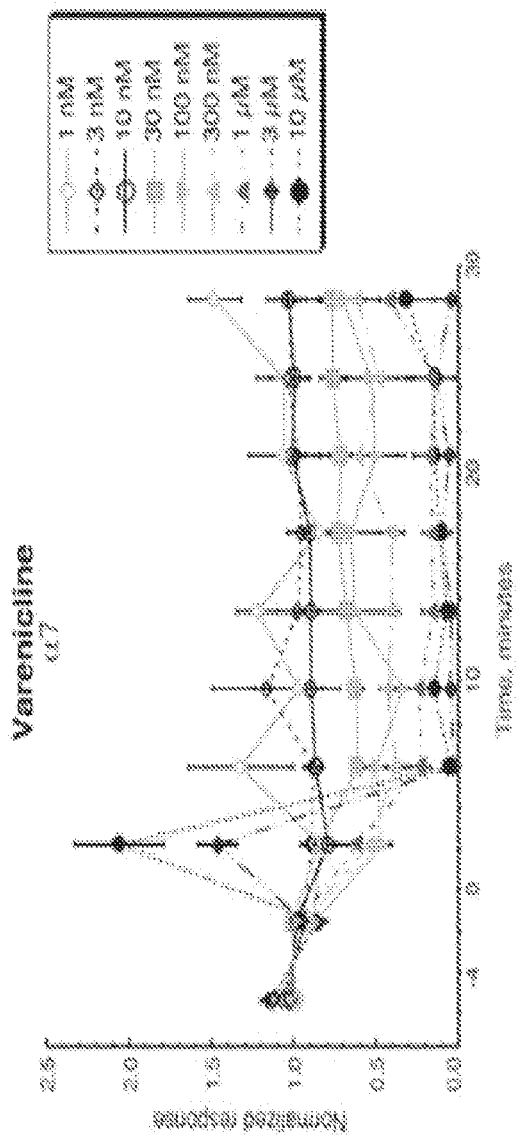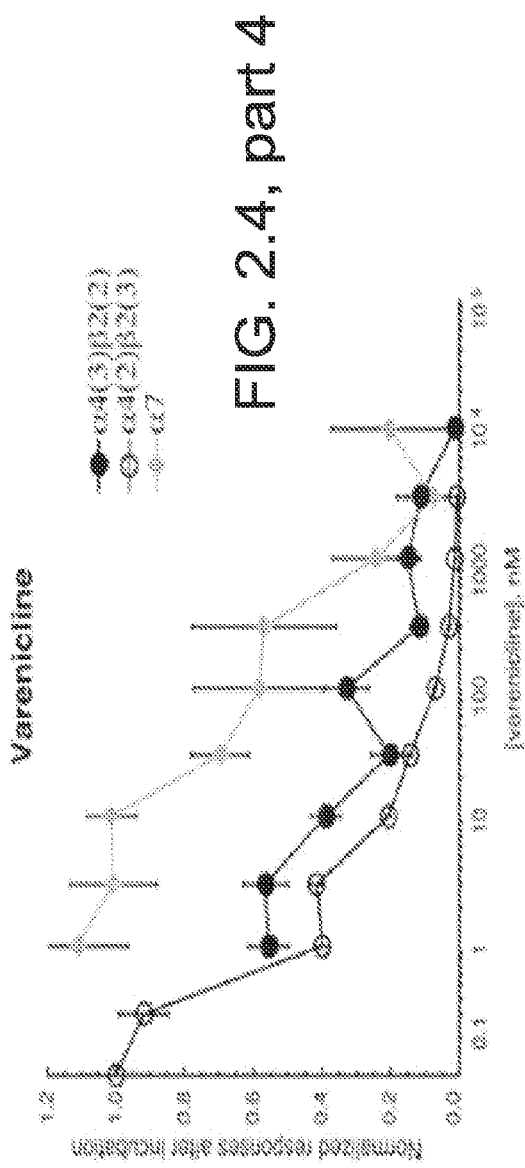
FIG. 2.4, part 4

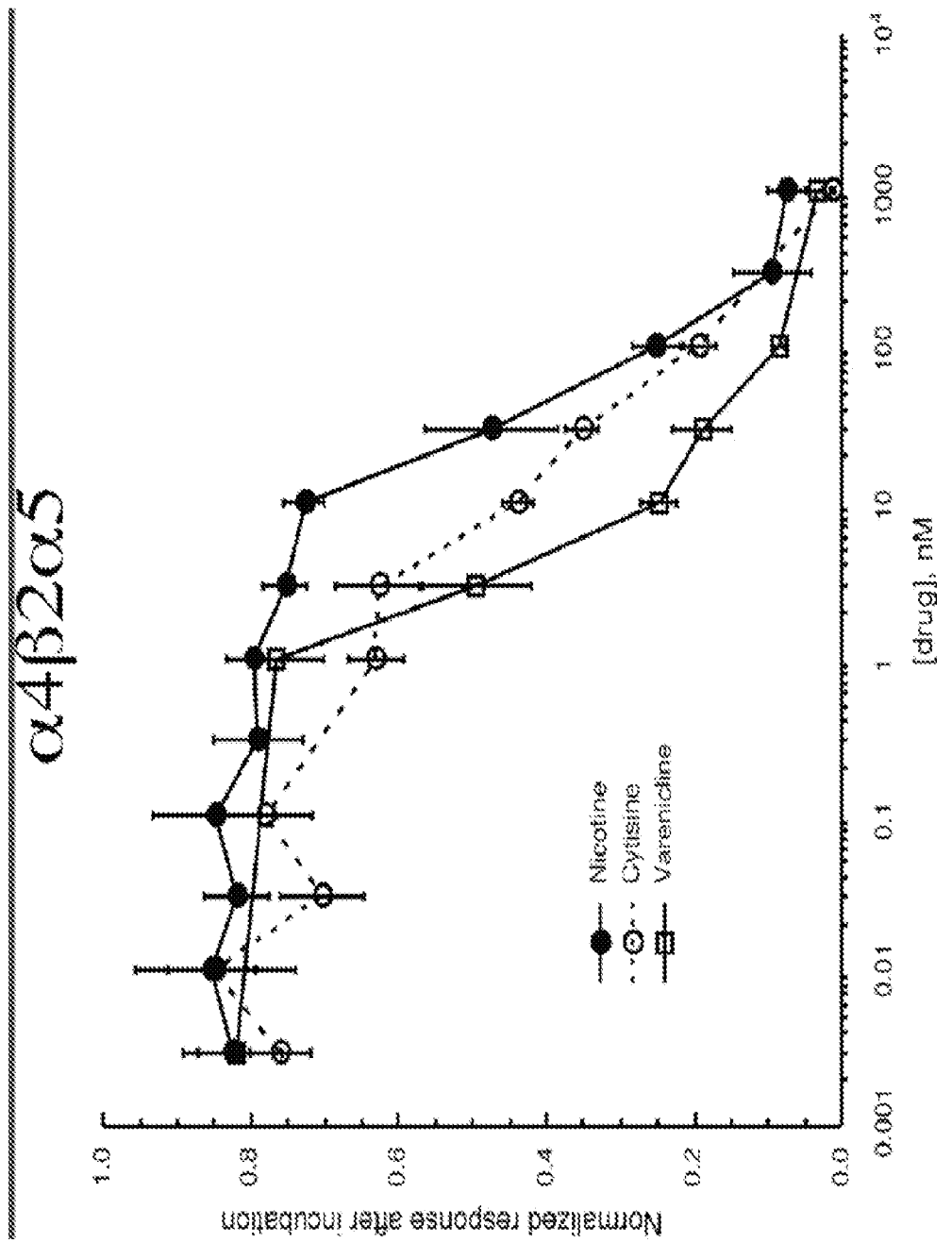
FIG. 2.5

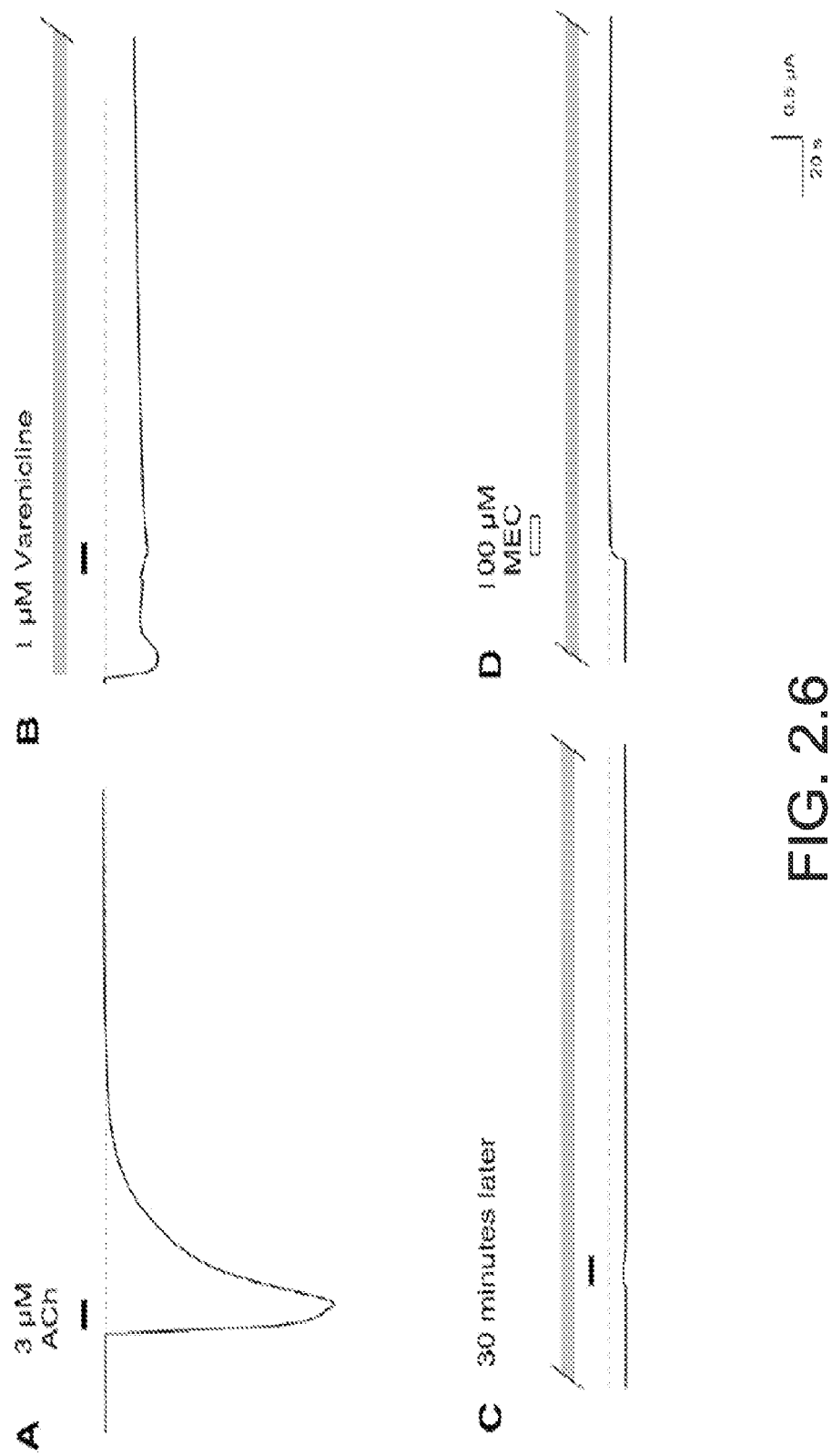
FIG. 2.6

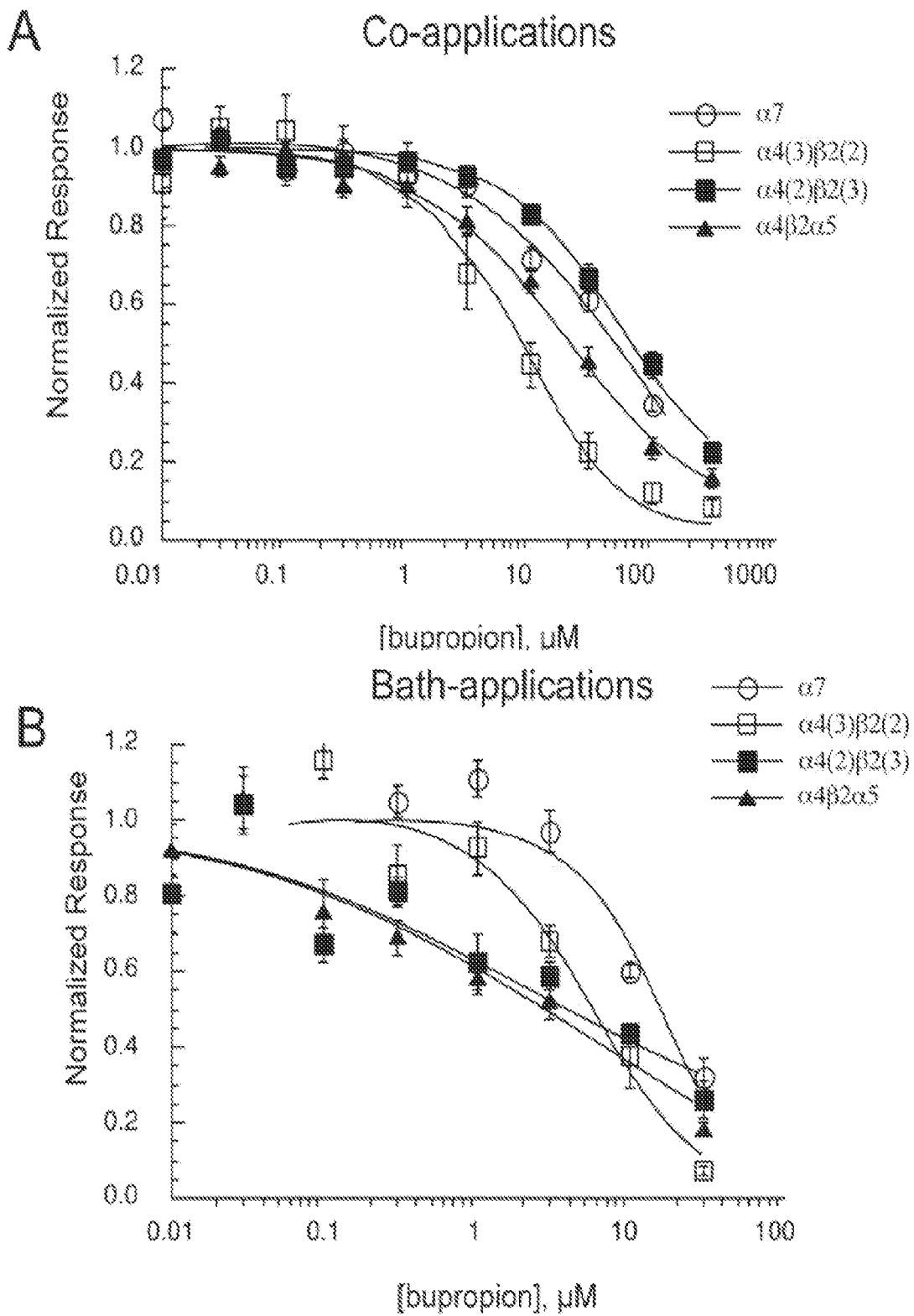
FIG. 2.7

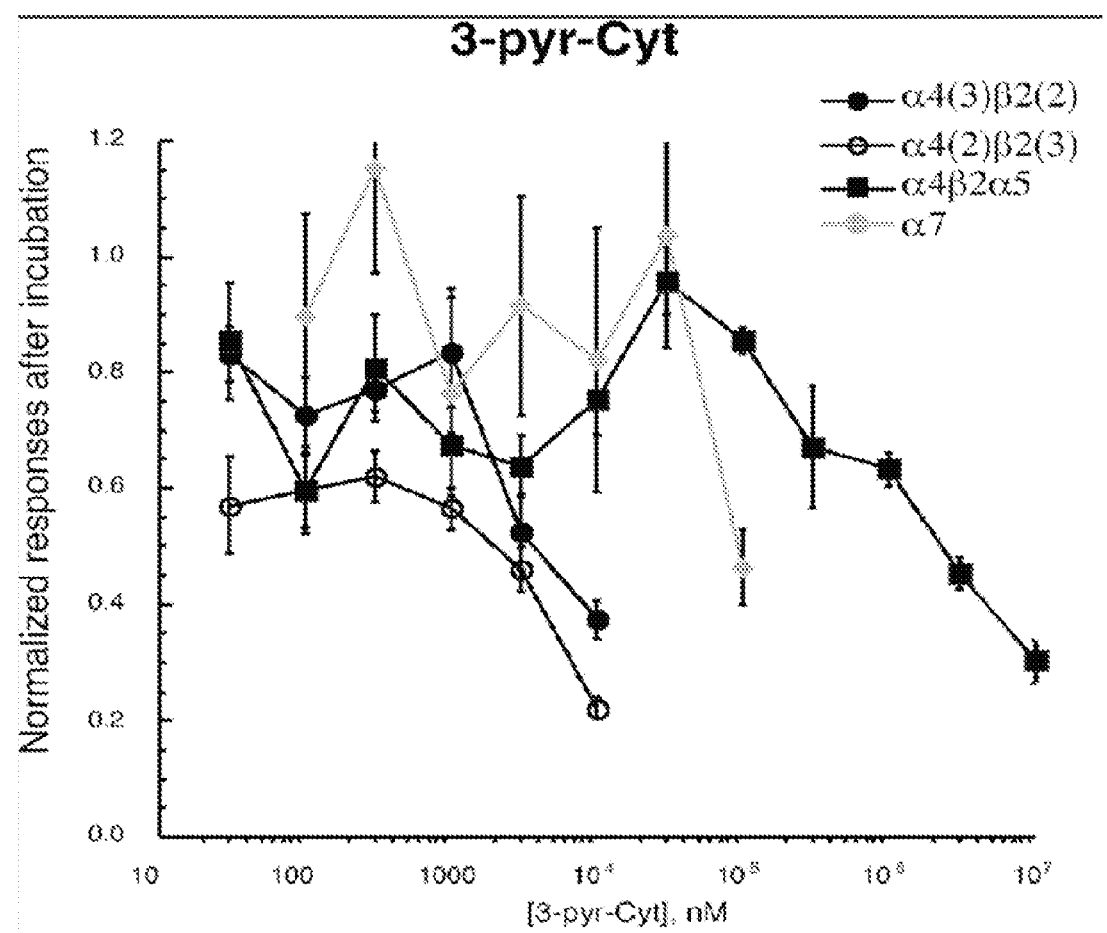
FIG. 2.8

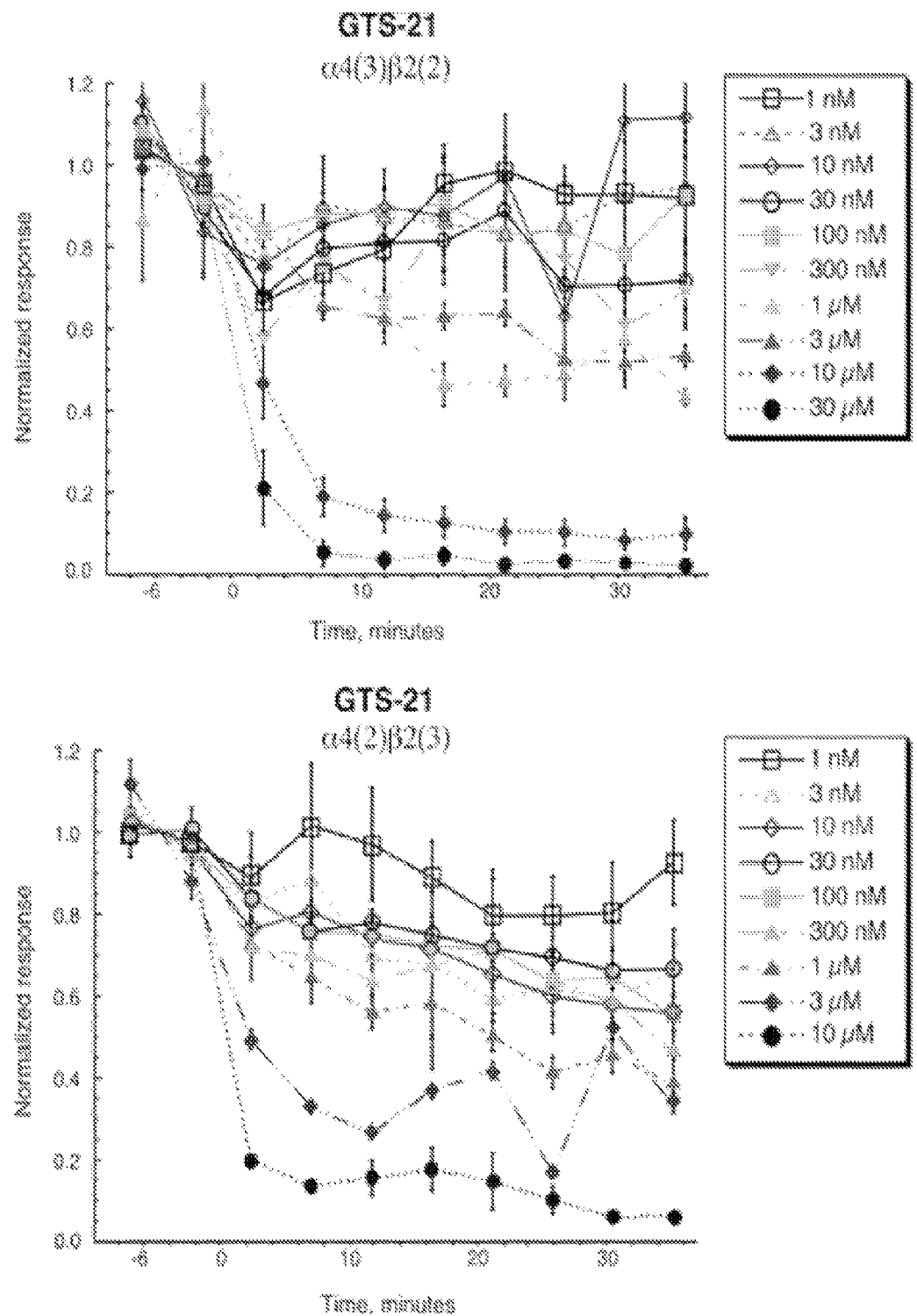
FIG. 2.9, part 1

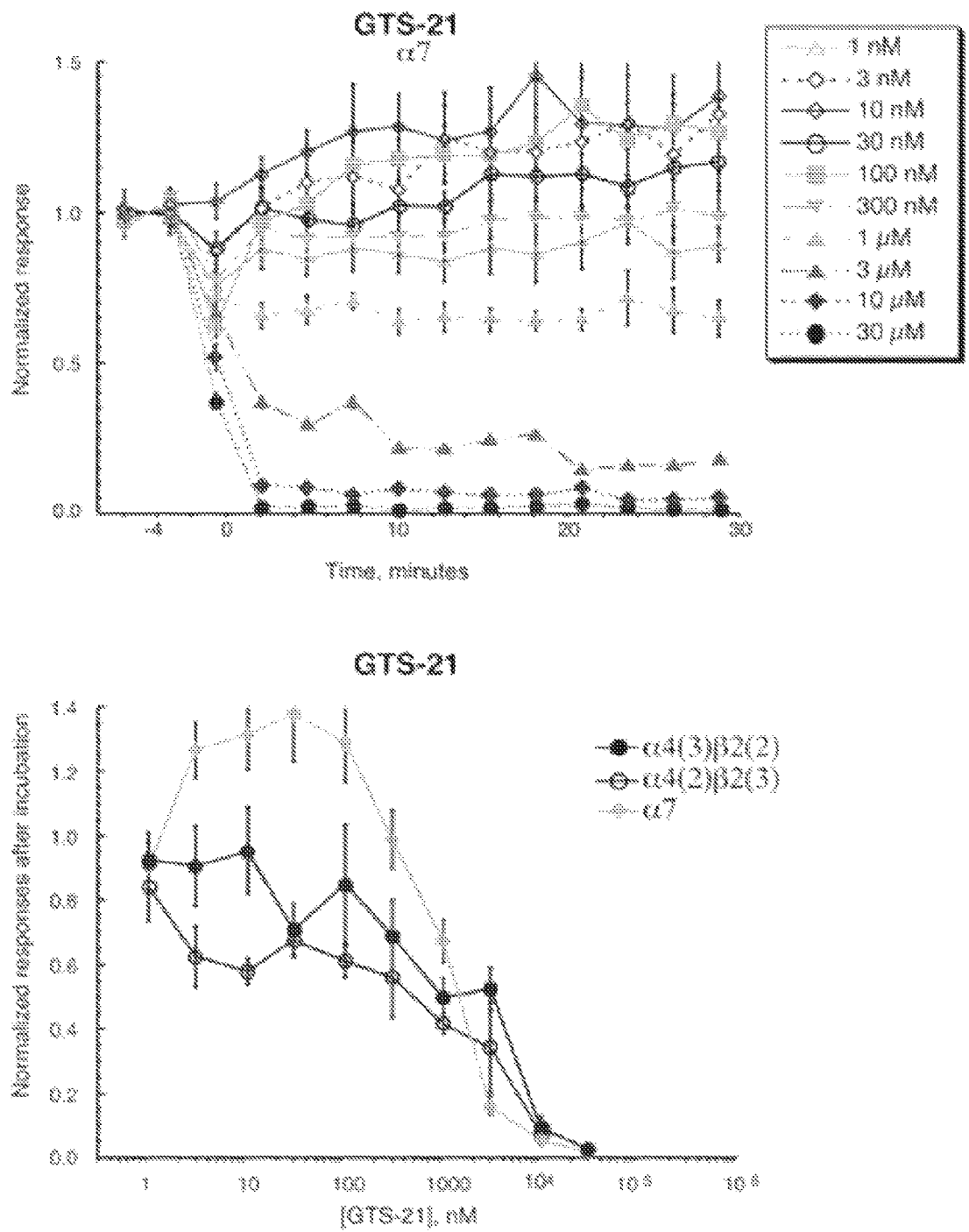
FIG. 2.9, part 2

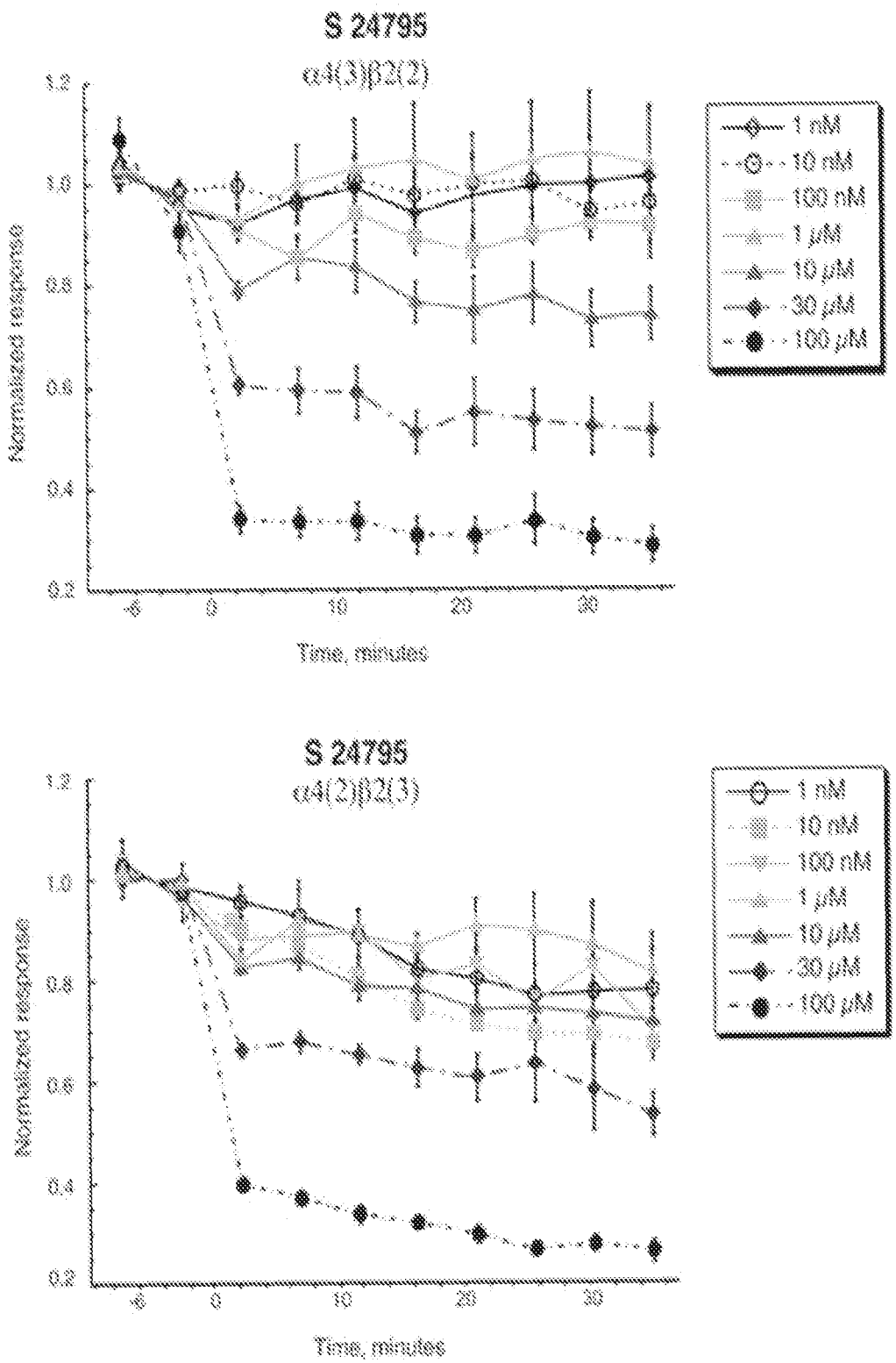
FIG. 2.10, part 1

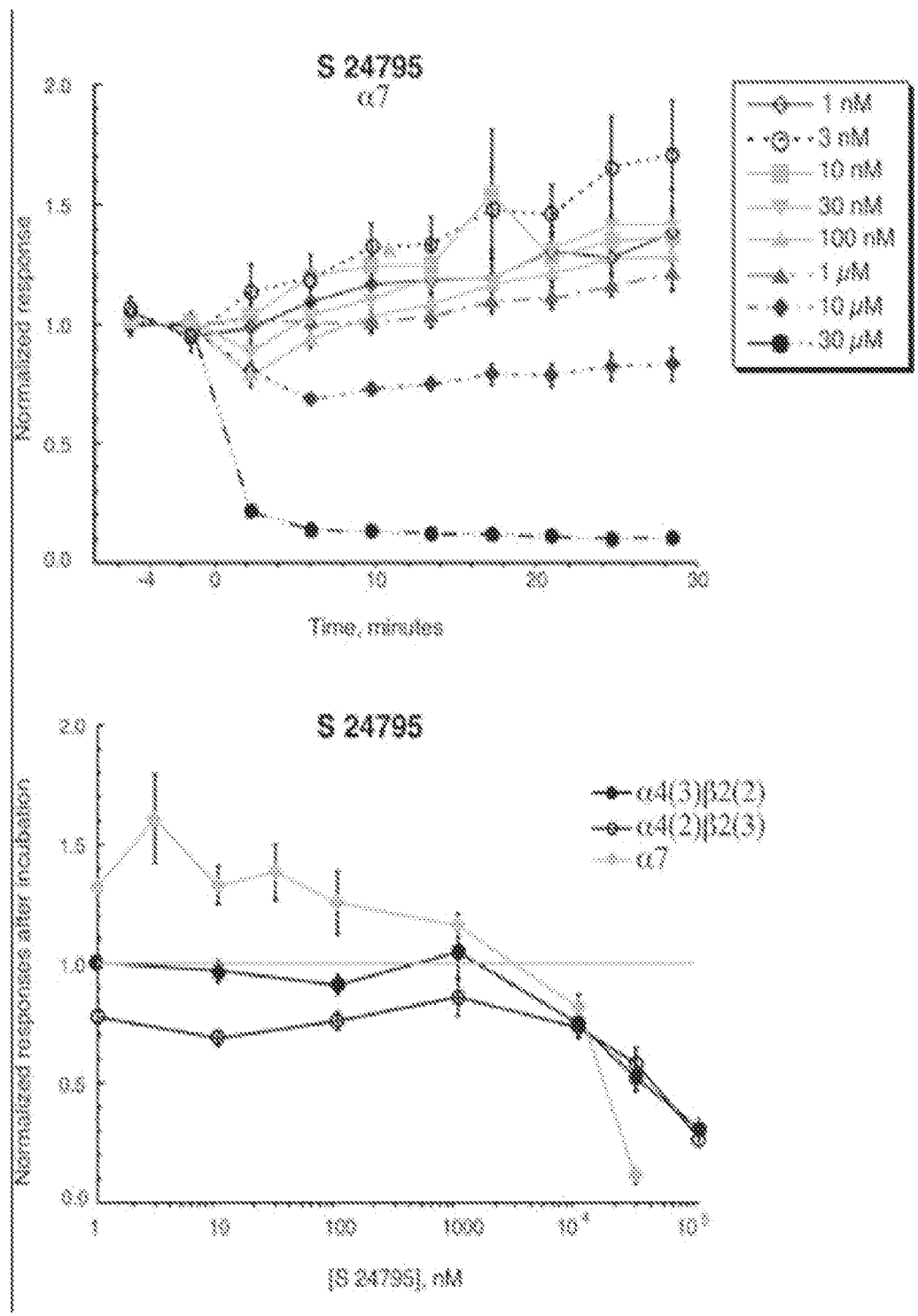
FIG. 2.10, part 2

COMPOSITIONS, METHODS OF USE, AND METHODS OF TREATMENT

CROSS-REFERENCE TO RELATED APPLICATIONS

This application is the 35 U.S.C. §371 national stage of PCT application PCT/US2011/33574, filed Apr. 22, 2011, which claims priority to and the benefit of U.S. Provisional Application No. 61/327,321, filed Apr. 23, 2010, both of which are hereby incorporated by reference in their entirety.

FEDERAL SPONSORSHIP

This invention was made with Government support under Contract/Grant No. R01GM57481, awarded by the National Institutes of Health. The Government has certain rights in this invention.

BACKGROUND

The armamentarium of pharmacotherapeutics includes agonists (receptor activators), and antagonists (inhibitors of receptor activation). However, many drugs fall in between these two categories and are classified as partial agonists. In therapeutic applications, a partial agonist can act as a sort of activity buffer for naturally occurring strong agonists, providing receptor stimulation if the natural activator is low or absent, and diminishing the effects of a natural strong activator if the strong activator's concentrations are high.

Partial agonists may also be used to buffer the effects of drugs of abuse; an area of current interest for the development of partial agonist therapies is for the treatment of nicotine addiction and dependence. A new drug in this area is the cytisine-related compound, varenicline (®Chantix). Varenicline is a weak partial agonist for nicotinic acetylcholine receptor (nAChR) subtypes in the brain that contain $\alpha 4$ and $\beta 2$ subunits, which have been shown in animal studies to be essential for nicotine to stimulate the brain's neurochemical reward systems. However, varenicline will also further decrease the function of $\alpha 7$ receptors in neuropsychiatric patients. Reports of suicide and worsened depressions in patients taking varenicline has led the FDA to issue a black box warning on the drug. Thus, using varenicline by itself is not a satisfactory solution for many individuals suffering from nicotine dependence. Consequently, other solutions are desirable.

SUMMARY

Briefly described, embodiments of this disclosure, among others, include compositions, pharmaceutical compositions, methods of treating nicotine dependence, methods of treating a subject who smokes and has a risk for depression or other neuropsychiatric disorder, method of treating a subject who smokes and has a risk for depression or other neuropsychiatric disorders, and the like.

One exemplary composition, among others, includes: a $\alpha 7$-selective partial agonist and a $\alpha 4 \beta 2$ partial agonist or a salt of one or both of the $\alpha 7$-selective partial agonist and the $\alpha 4 \beta 2$ partial agonist.

One exemplary pharmaceutical composition, among others, includes: a therapeutically effective amount of each of a $\alpha 7$-selective partial agonist and a $\alpha 4 \beta 2$ partial agonist, or a pharmaceutically acceptable salt of one or both of the $\alpha 7$-selective partial agonist and the $\alpha 4 \beta 2$ partial agonist, and a pharmaceutically acceptable carrier.

One exemplary method of treating nicotine dependence, among others, includes: delivering to a subject in need thereof, a pharmaceutical composition, wherein the pharmaceutical composition includes a therapeutically effective amount of each of a $\alpha 7$-selective partial agonist and a $\alpha 4 \beta 2$ partial agonist, or a pharmaceutically acceptable salt of one or both of the $\alpha 7$-selective partial agonist and the $\alpha 4 \beta 2$ partial agonist, and a pharmaceutically acceptable carrier.

One exemplary method of treating nicotine dependence, among others, includes: delivering to a subject in need thereof, a therapeutically effective amount of both a $\alpha 7$-selective partial agonist and a $\alpha 4 \beta 2$ partial agonist or a pharmaceutically acceptable salt of one or both of the $\alpha 7$-selective partial agonist and the $\alpha 4 \beta 2$ partial agonist.

One exemplary method of treating a subject who smokes and has a risk for depression or other neuropsychiatric disorder, among others, includes: delivering to a subject in need thereof, a pharmaceutical composition, wherein the pharmaceutical composition includes a therapeutically effective amount of each of a $\alpha 7$-selective partial agonist and a $\alpha 4 \beta 2$ partial agonist, or a pharmaceutically acceptable salt of one or both of the $\alpha 7$-selective partial agonist and the $\alpha 4 \beta 2$ partial agonist, and a pharmaceutically acceptable carrier.

Other compositions, methods, features, and advantages of this disclosure will be or become apparent to one with skill in the art upon examination of the following drawings and detailed description. It is intended that all such additional compositions, methods, features, and advantages be included within this description, be within the scope of this disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1.1 illustrates the effects of bath applications of partial agonists on Ach-evoked responses of nAChR expressed in *Xenopus* oocytes. The left most plot shows the effect of long-term application of GTS-21 (1 nM to 30 µM) on $\alpha 7$ (net charge responses). Responses were inhibited at concentrations greater than 300 nM, and potentiated at concentrations <30 nM. The two plots on the right show the effects of bath-applied nicotine (1 nM to 1 µM) on the Ach-evoked responses of HS$\alpha 4(2)\beta 2(3)$ and LS$\alpha 4(3)\beta 2(2)$ receptors. LS receptors appear less sensitive to low and intermediate concentrations of nicotine than HS receptors.

FIG. 1.2 illustrates the effects of 30 minute bath applications of GTS-21 or varenicline on the ACh-evoked responses of human $\alpha 7$ or $\alpha 4 \beta 2$ nAChR. The data are the average of responses obtained 30, 35 and 40 minutes after the addition of the experimental partial agonists to the bath. The $\alpha 7$ data are measurement of net charge, the data on the two forms of $\alpha 4 \beta 2$ are for peak current amplitude. Data are expressed relative to the amplitude of ACh controls obtained 2 and 7 minutes before the start of the bath applications Indicated by the gray lines in the plots.

FIG. 2.1 illustrates a model applied to the activation of nAChR by simultaneous co-applications of the full agonist "a" and a partial agonist "p". The terms are defined as follows: [a], concentration of ACh; concentration of the partial agonist, (either S 24795 or cytisine in FIG. 2.2A or 2.2B, respectively); [a+p], the sum of the concentrations; $n_a$, the Hill coefficient for ACh agonist activity; $n_p$, the Hill coefficient for partial agonist activity; $R_{maxP}$, the maximal agonist activity for the partial agonist relative to ACh; $EC_{50a}$, the $EC_{50}$ for ACh; $EC_{50p}$, the $EC_{50}$ for the partial agonist; $In_{maxP}$, the maximal inhibitory activity of the partial agonist; $IC_{50p}$, the $IC_{50}$ for the inhibitory effects of the partial agonist; $n_i$, the Hill coefficient for inhibition by the partial agonist. The $I_{Max}$ of the full agonist is assigned a value of 1. The first and second terms of the equation represent the activation produced by the full agonist and partial agonists, respectively, scaled by their potencies and weighted by receptor availability. The third term allows noncompetitive effects of the partial agonist. If such noncompetitive activity is inhibitory, then $n_i$ is assigned a negative value.

FIG. 2.2 illustrates the experimental (points) and predicted (lines) data for full and partial agonist interactions. FIG. 2.2A illustrates the observed experimental data for the net charge responses of α7-expressing cells to the co-applications of ACh and S 24795 across a range of concentrations are compared to the responses predicted by the model at the same concentrations. For clarity of presentation, half of the data representing responses obtained in progressively increasing concentration of S 24795 are shown in the left panel (from 0.1 µM to 1 mM, by factors of ten), while the other half of the data set are shown in the right panel (from 0.3 µM to 300 µM, by factors of ten). FIG. 2.2B illustrates the experimental data for the peak current responses of cells expressing the α4(3)β2(2) form of α4β2 to co-applications of ACh and cytisine across a range of concentrations are compared to the responses predicted by the model at the same concentrations. For clarity of presentation, half of the data representing responses obtained in progressively increasing concentration of cytisine are shown in the left panel (from 0.1 µM to 1 mM, by factors of ten), while the other half of the data set are shown in the right panel (from 0.3 µM to 300 µM, by factors of ten). For an alternative presentation of these data as pseudo 3-D plots go to the on-line supplemental data.

FIG. 2.3 illustrates the effects of bath-applied nicotine on the ACh-evoked responses of α4β2 and α7 nAChR. Pure populations of α4(3)β2(2) and α4(2)β2(3) nAChR were obtained by co-expressing the β2-6-α4 concatamer with monomeric α4 or β2, respectively. After measuring two baseline ACh-evoked responses, the α4β2 partial agonists were added to the bath solution, and the cells were repeatedly probed for their ACh responses. The ranges of nicotine concentrations tested were 1 nM to 3 µM and 0.3 nM to 3 µM for α4(3)β2(2) and α4(2)β2(3), respectively, and 1 nM to 10 µM for α7. All points represent an average of at least four oocytes (±SEM) for each condition. The summary at the last displays the average of the last three responses in the upper graphs, plotted as functions of the bath concentrations applied.

FIG. 2.4 illustrates the effects of bath-applied cytisine and varenicline on the ACh-evoked responses of α4β2 and α7 nAChR. Pure populations of α4(3)β2(2) and α4(2)β2(3) nAChR were obtained by co-expressing the β2-6-α4 concatamer (Zhou et al., 2003) with monomeric α4 or β2, respectively. After measuring two baseline ACh-evoked responses, the α4β2 partial agonists were added to the bath solution, and the cells were repeatedly probed for their ACh responses at 223 s (α7) or 277 s (non-α7) intervals. The ranges of cytisine concentrations tested were: 0.03 nM to 3 µM for both α4(3)β2(2) and α4(2)β2(3), and 1 nM to 1 µM for α7. The ranges of varenicline concentrations tested were 1 nM to 19 µM and 0.01 nM to 3 µM for α4(3)β2(2) and α4(2)β2(3), respectively, and 1 nM to 10 µM for α7. All points represent an average of at least four oocytes (±SEM) for each condition. The summaries at the bottom display the average of the last three responses in the upper graphs, plotted as functions of the bath concentrations applied.

FIG. 2.5 illustrates a summary of effects obtained with α4β2α5 nAChR. Pure populations α4β2α5 nAChR were obtained by co-expressing the β2-6-α4 concatamer with monomeric α5 (Kuryatov et al., 2008). Bath application experiments were conducted as described for the α4(2)β2(3) and α4(3)β2(2) receptors (FIGS. 2.4 & 2.5). This summary shows the average of the three responses obtained after nicotine or the cytisine-related compounds were in the bath for 30±4 minutes.

FIG. 2.6 illustrates effects of mecamylamine on steady-state baseline current of α4β2α5 receptors stimulated by bath-applied varenicline. FIG. 2.6A illustrates the prior to the addition of varenicline to the bath, application of 3 µM ACh (black bar) produced a large transient current, as illustrated by the representative response. FIG. 2.6B illustrates the bath application of 1 µM varenicline (gray bar) stimulated a response that appeared as a sustained shift in baseline current. The presence of 1 µM varenicline in the bath also had the effects of suppressing the transient response to an application of 3 µM ACh (black bar). FIG. 2.6C illustrates that after 30 minutes of continuous varenicline bath application, the baseline current remained elevated and ACh-evoked responses were suppressed. FIG. 2.6D illustrates that after 30 minutes of continuous varenicline bath application, 100 µM mecamylamine was applied (open bar), which reduced the baseline current to the original control level, indicating that the baseline shift was caused by steady-state activation of α4β2α5 nAChR.

FIG. 2.7 illustrates the effects of bupropion on the ACh-evoked responses of nAChR. FIG. 2.7A shows bupropion was co-applied with ACh and the evoked responses were calculated relative to the responses to ACh applied alone. FIG. 2.7B illustrates the effects of bath-applied Bupropion on the ACh-evoked responses of α4β2 and α7 nAChR. Pure populations of α4(3)β2(2) and α4(2)β2(3) and α4β2α5 nAChR were obtained by co-expressing the β2-6-α4 concatamer (Zhou et al., 2003) with monomeric α4, β2, or α5, respectively. After measuring two baseline ACh-evoked responses, bupropion was added to the bath solution, and the cells were repeatedly probed for their ACh responses. The plot displays the average of three responses obtained after bupropion had been in the bath for 30 minutes, plotted as functions of the bath concentrations applied. All points represent an average of at least four oocytes (±SEM) for each condition.

FIG. 2.8 is a summary of the effects of bath-applied 3-pyr-Cyt on α4(3)β2(2) and α4(2)β2(3) and α7 nAChR. Bath application experiments were conducted as described for cytisine, varenicline, and nicotine. This summary shows the average of the three responses obtained after 3-pyr-Cyt was in the bath for 30±4 minutes.

FIG. 2.9 illustrates the effects of bath-applied GTS-21 on the ACh-evoked responses of α4β2 and α7 nAChR. Pure populations of α4(3)β2(2) and α4(2)β2(3) nAChR were obtained by co-expressing the β2-6-α4 concatamer (Zhou et al., 2003) with monomeric α4 or β2, respectively. After measuring two baseline ACh-evoked responses, the α7-selective partial agonist was added to the bath solution, and the cells were repeatedly probed for their ACh responses. The ranges of GTS-21 concentrations tested were 1 nM to 30 µM and 1 nM to 10 µM for α4(3)β2(2) and α4(2)β2(3), respectively, and 1 nM to 30 µM for α7. All points represent an average of at least four oocytes (±SEM) for each condition. The summary at the bottom displays the average of the last three responses in the upper graphs, plotted as functions of the bath concentrations applied.

FIG. 2.10 illustrates the effects of bath-applied S 24795 on the ACh-evoked responses of $\alpha 4\beta 2$ and $\alpha 7$ nAChR. Pure populations of $\alpha 4(3)\beta 2(2)$ and $\alpha 4(2)\beta 2(3)$ nAChR were obtained by co-expressing the $\beta 2$-6-$\alpha 4$ concatamer (Zhou et al., 2003) with monomeric $\alpha 4$ or $\beta 2$, respectively. After measuring two baseline ACh-evoked responses, the $\alpha 7$-selective partial agonist was added to the bath solution, and the cells were repeatedly probed for their ACh responses. The ranges of S 24795 concentrations tested were 1 nM to 100 µM for $\alpha 4(3)\beta 2(2)$ and $\alpha 4(2)\beta 2(3)$, and 1 nM to 30 µM for $\alpha 7$. All points represent an average of at least four oocytes (±SEM) for each condition. The summary at the bottom displays the average of the last three responses in the upper graphs, plotted as functions of the bath concentrations applied.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Definitions:

Unless otherwise defined, all technical and scientific terms used herein have the same meaning as commonly understood by one of ordinary skill in the art of molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease, i.e., infection, being treated, and/or that amount that will prevent, to some extent, one or more of the symptoms of the disease, i.e., infection, that the host being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a composition may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of 13-Lactam antibiotics, Pharm. Biotech. 11,: 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al.

(1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing an agent of the present disclosure into a host. One preferred route of administration of the agents is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a tumor, a disease or a disorder with an agent to affect the disease or disorder by improving or altering it. The improvement or alteration may include an improvement in symptoms or an alteration in the physiologic pathways associated with the tumor, disease, or disorder. "Treatment," as used herein, covers one or more treatments of a tumor or a disease in a host (e.g., a mammal, typically a human or non-human animal of veterinary interest), and includes: (a) reducing the risk of occurrence of the disease in a subject determined to be predisposed to the tumor or disease but not yet diagnosed with it (b) impeding the development of the tumor or disease, and/or (c) relieving the tumor disease, e.g., causing regression of the tumor or disease and/or relieving one or more disease symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a tumor, a disease, or a symptom thereof and/or may be therapeutic in terms of a partial or complete cure for a tumor, a disease, and/or adverse effect attributable to the disease.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

Discussion:

The present disclosure provides compositions, pharmaceutical compositions, methods of treatment of nicotine dependence (smoking), methods of treatment using compositions or pharmaceutical compositions, and the like. Embodiments of the present disclosure can include treatment of nicotine dependence using the combination of a $\alpha 7$-selective partial agonist (e.g., 3-(2,4-dimethoxybenzylidene)anabaseine (DiMeOBA) (GTS-21), which has been approved for human studies)) and a $\alpha 4 \beta 2$ partial agonist (e.g., varenicline, which approved to treat nicotine dependence). The $\alpha 7$-selective partial agonist and the $\alpha 4 \beta 2$ partial agonist could be separately delivered (e.g., separate compositions) or can be delivered in combination in a composition or pharmaceutical composition. An advantage of the combination of the $\alpha 7$-selective partial agonist and the $\alpha 4 \beta 2$ partial agonist is that it provides synergistic effects that lessen depression while improving compliance for smoking cessation in subjects at risk for depression or other neuropsychiatric disorders. Additional details are described in the Examples.

Nicotine binds to two primary types of nicotinic acetylcholine receptors (nAChR) in the brain. One type, $\alpha 4 \beta 2^*$, is associated with addiction and dependence. The other type, $\alpha 7$ is not associated with nicotine addiction in normal individuals, but has been shown to be decreased under stressful conditions and to have diminished function in neuropsychiatric populations. Smoking is more common in people with depression and other neuropsychiatric conditions than in the general population. It is believed that for these individuals, smoking is driven by a desire to self-medicate through the stimulation of the diminished $\alpha 7$ receptors, as well as by the changes in $\alpha 4 \beta 2^*$ receptors normally associated with nicotine dependence.

As mentioned above, the most recently developed approach for helping people quit smoking has been to use a drug (varenicline/Chantix®) which is a weak stimulator of the $\alpha 4 \beta 2^*$ receptors. Varenicline (7,8,9,10-tetrahydro-6,10-methano-6H-pryazino (2,3-h)(3) benzazepine) is believed to partially replace and otherwise suppress the rewarding effects of nicotine mediated by $\alpha 4 \beta 2^*$ receptors. However, varenicline has disadvantages for neuropsychiatric patients and there are reports of suicide and worsened depressions in patients taking varenicline. Thus, using varenicline by itself is not a satisfactory solution for many individuals suffering from nicotine dependence.

It has been shown that DiMeOBA (GTS-21) is a selective partial activator of $\alpha 7$ receptors. GTS-21 is an approved drug for human studies and is currently in clinical trials for schizophrenia. Embodiments of the present disclosure contemplate that GTS-21, or a comparable $\alpha 7$-selective partial agonist, would be efficacious as an adjunct therapy to varenicline (or comparable $\alpha 4 \beta 2$ partial agonist), to lessen depression and improve compliance for smoking cessation in a patient population at high risk for depression or other neuropsychiatric disorders. As described herein, this is supported by showing that at low concentration, bath applications of GTS-21 (or potentially other weak $\alpha 7$-selective partial agonists) can potentiate the ACh-evoked responses of $\alpha 7$ nAChR and would synergize with $\alpha 4 \beta 2$ partial agonists to decrease the function of $\alpha 4 \beta 2^*$ nAChR. Thus, in contrast to using varenicline alone, embodiments of the present disclosure provide an alternative for treating nicotine dependence that overcomes the deficiencies of varenicline alone. Additional details are described in the Examples.

In an embodiment, the $\alpha 7$-selective partial agonist can include nicotinic agonists or a salt thereof (e.g., a pharmaceutically acceptable thereof). In an embodiment, the $\alpha 7$-selective partial agonist can include compounds such as quinuclidines, tropan-like compounds, cytisine-like compounds, nicotine-like, anabaseines, pyrrolidines, piperidines, linear amines, and azobicyclics, or any pharmaceutical acceptable salt of any of these, including any polymorph or any prodrug thereof, or any pharmaceutically acceptable salt of such a prodrug. Exemplar compounds include those described in Horenstein et al., *Molecular Pharmacology*, 74(6):1496-511 (See, circled compounds in FIG. 1 of this paper), which is incorporated herein by reference, or any pharmaceutical acceptable salt thereof, including any polymorph or any prodrug thereof, or any pharmaceutically acceptable salt of such a prodrug. In an embodiment, the α7-selective partial agonist can include those described in U.S. Pat. Nos. 5,516,785 and 6,630,491, each of which is incorporated by reference. In particular, the α7-selective partial agonist is GTS-21 or any pharmaceutical acceptable salt thereof, including any polymorph or any prodrug thereof, or any pharmaceutically acceptable salt of such prodrug, which is described in these patents.

In an embodiment, the α4β2 partial agonist can include nicotinic agents or a salt thereof (e.g., a pharmaceutically acceptable thereof). In an embodiment, the α4β2 partial agonist can include compounds such as varenicline (7,8,9,10-tetrahydro-6,10-methano-6H-pyrazino (2,3-h)(3) benzazepine) or other cytisine derivatives including 3-(pyridine-3'-yl)-cytisine (3-pyr-Cyt), (See, Mineur et al., Journal of Pharmacology and Experimental Therapeutics, 329(1):377-86, which is incorporated here by reference), or any pharmaceutical acceptable salt of any of these, including any polymorph or any prodrug thereof, or any pharmaceutically acceptable salt of such a prodrug. In an embodiment, the α4β2 partial agonist can include compounds described in U.S. Pat. Nos. 6,410,550, 6,890,927, and 7,265,119, each of which is incorporated by reference. In particular, the α4β2 partial agonist is varenicline, or any pharmaceutical acceptable salt thereof, including any polymorph or any prodrug thereof, or any pharmaceutically acceptable salt of such prodrug. Varenicline and other possible α4β2 partial agonist may be described in U.S. Pat. Nos. 6,410,550, 6,890,927, and 7,265,119. A preferred salt of varenicline is varenicline tartrate. Synthesis of varenicline tartrate is disclosed in WO 99/35131, U.S. Pat. No. 6,410,550, Patent Application Nos. 1997070245, 2002072524, 2002072525, 2002111350, and 2002132824, each of which is incorporated herein by reference.

Methods of Use

Embodiments of this disclosure include methods of treating nicotine dependence using compositions and pharmaceutical compositions described herein. As noted above, the α7-selective partial agonist (e.g., DiMeOBA (GTS-21)) and the α4β2 partial agonist (e.g., varenicline) can be included in a single composition or in separate compositions. In an embodiment including separate compositions, the components can be given simultaneously or a different times, but are both administered in a time frame to realize the benefits of the using both partial agonists. Additional details are provided in the Examples.

It should be noted that the therapeutically effective amount to result in uptake of α7-selective partial agonist and the α4β2 partial agonist, in combination or separately, into the host will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Kits

The present disclosure also provides packaged compositions or pharmaceutical compositions comprising a pharmaceutically acceptable carrier and the α7-selective partial agonist (e.g., DiMeOBA (GTS-21)) and the α4β2 partial agonist (e.g., varenicline) of the disclosure for use in treating nicotine dependence. Other packaged compositions or pharmaceutical compositions provided by the present disclosure further include indicia including at least one of: instructions for using the composition to treat nicotine dependence. The kit can further include appropriate buffers and reagents known in the art for administering various combinations of the components listed above to the host.

Pharmaceutical Formulations and Routes of Administration

Embodiments of the present disclosure include the α7-selective partial agonist (e.g., DiMeOBA (GTS-21)) and the α4β2 partial agonist (e.g., varenicline), in combination or separately, identified herein and formulated with one or more pharmaceutically acceptable excipients, diluents, carriers and/or adjuvants. In addition, embodiments of the present disclosure include the α7-selective partial agonist (e.g., DiMeOBA (GTS-21)) and the α4β2 partial agonist (e.g., varenicline), in combination or separately, formulated with one or more pharmaceutically acceptable auxiliary substances. In particular, the α7-selective partial agonist (e.g., DiMeOBA (GTS-21)) and the α4β2 partial agonist (e.g., varenicline), in combination or separately, can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the α7-selective partial agonist (e.g., DiMeOBA (GTS-21)) and the α4β2 partial agonist (e.g., varenicline), in combination or separately, can be administered to the host using any means capable of resulting in the desired effect. Thus, the α7-selective partial agonist (e.g., DiMeOBA (GTS-21)) and the α4β2 partial agonist (e.g., varenicline), in combination or separately, can be incorporated into a variety of formulations for therapeutic administration. For example, the α7-selective partial agonist (e.g., DiMeOBA (GTS-21)) and the α4β2 partial agonist (e.g., varenicline), in combination or separately, can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the α7-selective partial agonist (e.g., DiMeOBA (GTS-21)) and the α4β2 partial agonist (e.g., varenicline), in combination or separately, may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, the α7-selective partial agonist (e.g., DiMeOBA (GTS-21)) and the α4β2 partial agonist (e.g., varenicline), in combination or separately, can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the α7-selective partial agonist (e.g., DiMeOBA (GTS-21)) and the α4β2 partial agonist (e.g., varenicline), in combination or separately, can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the α7-selective partial agonist (e.g., DiMeOBA (GTS-21)) and the α4β2 partial agonist (e.g., varenicline), in combination or separately, can be utilized in aerosol formulation to be administered via inhalation. Embodiments of the α7-selective partial agonist (e.g., DiMeOBA (GTS-21)) and the α4β2 partial agonist (e.g., varenicline), in combination or separately, can be formulated into pressurized acceptable propellants such as dichlorodifluoromethane, propane, nitrogen and the like.

Furthermore, embodiments of the α7-selective partial agonist (e.g., DiMeOBA (GTS-21)) and the α4β2 partial agonist (e.g., varenicline), in combination or separately, can be made into suppositories by mixing with a variety of bases such as emulsifying bases or water-soluble bases. Embodiments of the α7-selective partial agonist (e.g., DiMeOBA (GTS-21)) and the α4β2 partial agonist (e.g., varenicline), in combination or separately, can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more inhibiting agents. Similarly, unit dosage forms for injection or intravenous administration may comprise the α7-selective partial agonist (e.g., DiMeOBA (GTS-21)) and the α4β2 partial agonist (e.g., varenicline), in combination or separately, in a composition as a solution in sterile water, normal saline or another pharmaceutically acceptable carrier.

Embodiments of the α7-selective partial agonist (e.g., DiMeOBA (GTS-21)) and the α4β2 partial agonist (e.g., varenicline), in combination or separately, can be formulated in an injectable composition in accordance with the invention. Typically, injectable compositions are prepared as liquid solutions or suspensions; solid forms suitable for solution in, or suspension in, liquid vehicles prior to injection may also be prepared. The preparation may also be emulsified or the active ingredient (triamino-pyridine derivative and/or the labeled triamino-pyridine derivative) encapsulated in liposome vehicles in accordance with the present disclosure.

In an embodiment, the α7-selective partial agonist (e.g., DiMeOBA (GTS-21)) and the α4β2 partial agonist (e.g., varenicline), in combination or separately, can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the α7-selective partial agonist (e.g., DiMeOBA (GTS-21)) and the α4β2 partial agonist (e.g., varenicline), in combination or separately, can be accomplished using any of a variety of refillable, pump systems. Pumps provide consistent, controlled release over time. In some embodiments, the α7-selective partial agonist (e.g., DiMeOBA (GTS-21)) and the α4β2 partial agonist (e.g., varenicline), in combination or separately, can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., the α7-selective partial agonist (e.g., DiMeOBA (GTS-21)) and the α4β2 partial agonist (e.g., varenicline), in combination or separately,) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the α7-selective partial agonist (e.g., DiMeOBA (GTS-21)) and the α4β2 partial agonist (e.g., varenicline), in combination or separately, are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the α7-selective partial agonist (e.g., DiMeOBA (GTS-21)) and the α4β2 partial agonist (e.g., varenicline), in combination or separately, adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the α7-selective partial agonist (e.g., DiMeOBA (GTS-21)) and the α4β2 partial agonist (e.g., varenicline), in combination or separately, may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the α7-selective partial agonist (e.g., DiMeOBA (GTS-21)) and the α4β2 partial agonist (e.g., varenicline), in combination or separately, described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the α7-selective partial agonist (e.g., DiMeOBA (GTS-21)) and the α4β2 partial agonist (e.g., varenicline), in combination or separately, can be administered to a host in one or more doses. Those of skill will readily appreciate that dose levels can vary as a function of the specific the α7-selective partial agonist (e.g., DiMeOBA (GTS-21)) and the α4β2 partial agonist (e.g., varenicline), in combination or separately, administered, the severity of the symptoms and the susceptibility of the subject to side effects. Preferred dosages for a given compound are readily determinable by those of skill in the art by a variety of means.

In an embodiment, multiple doses of the α7-selective partial agonist (e.g., DiMeOBA (GTS-21)) and the α4β2 partial agonist (e.g., varenicline), in combination or separately, are administered. The frequency of administration of t the α7-selective partial agonist (e.g., DiMeOBA (GTS-21)) and the α4β2 partial agonist (e.g., varenicline), in combination or separately, can vary depending on any of a variety of factors, e.g., severity of the symptoms, and the like. For example, in an embodiment, the α7-selective partial agonist (e.g., DiMeOBA (GTS-21)) and the α4β2 partial agonist (e.g., varenicline), in combination or separately, can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the α7-selective partial agonist (e.g., DiMeOBA (GTS-21)) and the α4β2 partial agonist (e.g., varenicline), in combination or separately, is administered continuously.

The duration of administration of the α7-selective partial agonist (e.g., DiMeOBA (GTS-21)) and the α4β2 partial agonist (e.g., varenicline), in combination or separately, e.g., the period of time over which the α7-selective partial agonist (e.g., DiMeOBA (GTS-21)) and the α4β2 partial agonist (e.g., varenicline), in combination or separately, is administered, can vary, depending on any of a variety of factors, e.g., patient response, etc. For example, the α7-selective partial agonist (e.g., DiMeOBA (GTS-21)) and the α4β2 partial agonist (e.g., varenicline), in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the α7-selective partial agonist (e.g., DiMeOBA (GTS-21)) and the α4β2 partial agonist (e.g., varenicline), in combination or separately,) to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the α7-selective partial agonist (e.g., DiMeOBA (GTS-21)) and the α4β2 partial agonist (e.g., varenicline), in combination or separately,) can be administered in a single dose or in multiple doses.

Embodiments of the α7-selective partial agonist (e.g., DiMeOBA (GTS-21)) and the α4β2 partial agonist (e.g., varenicline), in combination or separately, can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the α7-selective partial agonist (e.g., DiMeOBA (GTS-21)) and the α4β2 partial agonist (e.g., varenicline), in combination or separately. Where systemic delivery is desired, administration typically involves invasive or systemically absorbed topical or mucosal administration of pharmaceutical preparations.

The α-selective partial agonist (e.g., DiMeOBA (GTS-21)) and the α4β2 partial agonist (e.g., varenicline), in combination or separately, can also be delivered to the subject by enteral administration. Enteral routes of administration include, but are not limited to, oral and rectal (e.g., using a suppository) delivery.

Methods of administration of the α7-selective partial agonist (e.g., DiMeOBA (GTS-21)) and the α4β2 partial agonist (e.g., varenicline), in combination or separately, through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Brief Introduction:

Nicotine binds to two primary types of nicotinic acetylcholine receptors (nAChR) in the brain. One type, α4β2*, is associated with addiction and dependence. The other type, α7, is not associated with nicotine addiction in normal individuals but has been shown to be decreased under stressful conditions and to have diminished function in neuropsychiatric populations. Smoking is more common in people with depression and other neuropsychiatric conditions than in the general population. It is believed that for these individuals, smoking is driven by a desire to self-medicate through the stimulation of the diminished α7 receptors, as well as by the changes in α4β2* receptors normally associated with nicotine dependence. The most recently developed approach for helping people quit smoking has been to use a drug (varenicline/Chantix) which is a weak stimulator of the α4β2* receptors. Varenicline is believed to partially replace and otherwise suppress the rewarding effects of nicotine mediated by α4β2* receptors. However, varenicline will also further decrease the function of α7 receptors in neuropsychiatric patients. Reports of suicide and worsened depressions in patients taking varenicline has led the FDA to issue a black box warning on the drug. We have shown that DiMeOBA (GTS-21) is a selective partial activator of α7 receptors. GTS-21 is an approved drug for human studies and is currently in clinical trials for schizophrenia. The core hypothesis is that GTS-21, or a comparable α7-selective partial agonist would be efficacious as an adjunct therapy to varenicline (or comparable α4β2 partial agonist), to lessen depression and improve compliance for smoking cessation in a patient population at high risk for depression or other neuropsychiatric disorders. Another finding supporting this approach is that at low concentration, bath applications of GTS-21 (or potentially other weak α7-selective partial agonists) can potentiate the ACh-evoked responses of α7 nAChR and would synergize with α4β2 partial agonists to decrease the function of α4β2* nAChR.

Discussion:

Nicotinic Acetylcholine Receptors and Nicotine Addiction

The mediators of nicotine's cognitive and addictive effects are nicotinic acetylcholine receptors (nAChR), ion channel receptors normally activated by the neurotransmitter acetylcholine (ACh). All nAChRs are organized as pentameric complexes. Those which contain five identical subunits are classified as homomeric receptors. Heteromeric receptors contain specialized alpha and non-alpha subunits. The heteromeric receptors can be further classified as either neuromuscular or neuronal, based on their cellular locations. The most important form of homomeric receptors are those that contain α7 subunits, and α7 receptors may be found in both neurons and non-neuronal cells.

Heteromeric neuromuscular nAChR are essential for muscle function and are relatively insensitive to nicotine. There are multiple subtypes of heteromeric neuronal nAChR that are sensitive to nicotine; specific subtypes in the brain, most importantly those containing α4 and β2 subunits (sometimes in combination with α6 or α5), are believed to be responsible for the addicting properties of nicotine [1, 2]. Stimulation of these receptors increases levels of the reward-associated neurochemical dopamine in the brain. Therefore α4β2-containing nAChR are principle targets for therapies to promote smoking cessation. However, nicotine is also an efficacious activator and desensitizer of the homomeric α7-type receptors.

Therapeutic Significance Associated with Multiple Nachr Subtypes in the Brain:

The α7 neuronal nAChRs are sites for high affinity a-bungarotoxin (α-btx) binding in the brain and are of roughly equal abundance to the high-affinity nicotine-binding sites, which are primarily composed of α4 and β2 subunits [3]. The α7 nAChR has a number of unique physiological and pharmacological properties that distinguish it, including a high permeability to calcium ($P_{ca}$:$P_{Na}$ of ≈10), rapid and reversible desensitization, and pronounced inward rectification [4]. The α7 subunit is expressed at high levels in the hippocampus and hypothalamus [4, 5] and has also been shown to have functionally important expression in non-neuronal tissues, such as cells of the immune system [6]. α4β2 receptors expressed in *Xenopus* oocytes have functional properties which correspond well to those of the predominant nAChR-mediated responses of cultured hippocampal neurons [7-11], mammalian cell lines [12], and native neuronal tissues [13].

In addition to diversity arising from multiple possible combinations of different subunits, even in receptors containing just single types of alpha and beta subunits (e.g. α4 and β2), the ratio of alpha to beta subunits in the pentamer is functionally important and may be regulated by tissue factors and exposure to ligands such as nicotine [14]. It has recently been established that α4β2 receptors with a stoichiometry of α4(2)β2(3) have a higher apparent sensitivity to nicotine and other agonists and lower calcium permeability than do receptors with a stoichiometry of α4(3)β2(2) [15]. In many tissues, the α4β2 receptor population is mixed, so that functional responses are best fit to a two-site model with high sensitivity (HS) α4β2 (presumably α4(2)β2(3)) and low sensitivity (LS) α4β2 (presumably α4(3)β2(2)) components [16]. Through the use of a linked β2-α4 subunit concatamer, relatively pure populations of HS or LS α4β2 receptors can be obtained in the oocyte expression system by co-expressing the concatamer with either monomeric β2 or α4 subunits, respectively [17]. It should also be noted that, although homomeric receptors are the primary functional form of α7 nAChR in the brain, atypical α7β2 heteromeric receptors may also exist in restricted brain areas [14].

nAChR Function in the Brain

There is scant evidence that nAChR mediate fast synaptic transmission in the brain and vastly more evidence that they modulate synaptic function mediated by other neurotransmitters [18-22]. nAChRs on nerve cell bodies appear to be diffuse over the cell surface and not associated with either pre- or post-synaptic specializations [23-26]. ACh seems to be released diffusely and subsequently binds to the various populations of presynaptic, perisynaptic, and somatic receptors [27], however, it remains unknown how high local concentrations of ACh become in the brain, or how long the cholinergic signals persist. Our general lack of knowledge about the nature of cholinergic signals presented to nAChR in the brain, and the absence of cholinergic synapses that can be readily studied in the brain, leaves us with having to approach the physiological characterization of these receptors with indirect means or through the expression of the receptors in artificial systems.

Nicotinic Ligands for Treatment of Addiction: Agonists, Partial Agonists, or Antagonists?

In the search for candidate drugs to treat nicotine dependence, of equal importance to understanding the functional properties of the specific nAChR in the brain responsible for addiction and dependence will be understanding how the candidate drugs function to either blunt or substitute for the nicotine reward. Certainly issues of pharmacokinetics, bioavailability, and brain penetration are important, and equally important is the question of which classes of drugs are likely to be the best candidates (reviewed in [28]). Nicotinic antagonists have been proposed as a treatment approach for nicotine addiction [29, 30] since they might be able to block nicotine reward. However, antagonist-based therapies also perturb endogenous cholinergic function, and so most approaches have focused on selective agonists and partial agonists.

For some neuronal nAChRs, nicotine is a full agonist, and so nicotine replacement therapies can be conceived as substituting one full agonist for another. However, in a therapeutic context, it must be considered that the presentation of an experimental agonist will not mimic the presentation of the natural activator ACh. For example, when an experimental drug is delivered by a pill, patch, or puff, levels of the drug in the hippocampus will not oscillate in the way that ACh levels will oscillate in response to rhythmic input from the septal cholinergic pathway [31-33]. Rather, the experimental drug will effectively be present at relatively steady levels, which may produce some equilibrium activation at certain concentrations, but may be predominantly desensitizing at other concentrations, thereby blunting the effects of the intrinsic cholinergic signals. Likewise, nicotine replacement therapies using slow nicotine delivery systems will not mimic the stimuli of the concentration changes produced by smoking [34].

In a therapeutic context, the effects of a partial agonist may be similar to those of a full agonist except that equilibrium activation would likely be lower and the blunting effects on other stimuli (including systemically administered nicotine, as well as endogenous ACh) would likely be greater [35]. A complicating factor is that specific drugs, such as varenicline, may be partial agonists for one receptor subtype and full agonists for other subtypes. Such a mixed activity profile may cause undesirable side effects.

The question of what sort of drug would be useful to treat nicotine addiction is further compounded by the fact that drugs may not only show selectivity for one nAChR subtype over another, but may also have different mechanisms of action on various receptor subtypes. Nicotine, itself, is a drug whose effects are fraught with such complications. Nicotine is a full agonist for some receptor subtypes and a partial agonist for others. Nicotine has also been reported to act as a noncompetitive antagonist, and to work not only on cell surface receptors but also to work intracellularly as a molecular chaperone, modulating the expression of specific receptor subtypes [36].

Varenicline and Other Cytisine Derivatives in Therapeutics:

Cytisine, a plant alkaloid, has been in use as a smoking cessation aid in Eastern Europe since the 1960's [37] and has been subsequently shown to be a partial agonist for heteromeric neuronal nAChR containing the β2 subunit [38]. Although the efficacy of cytisine for α4β2 receptors is low (<20% that of ACh), it also functions as a potent competitive antagonist, and [$^3$H]cytisine is a useful label to identify high affinity nicotine receptor in brain tissue [39]. However, the potential utility of cytisine as a therapeutic agent has been questioned [40] [37], due to a broad potential spectrum of side-effects and the low therapeutic index. More recently, the cytisine derivative, varenicline, which is also an α4β2 partial agonist, but active at other nAChRs as well [41], has been approved as a smoking cessation aid in the US and abroad (trade name Chantix).

The concept that an α4β2 partial agonist would have utility as a smoking cessation agent has relied variously on two hypotheses that have not yet been rigorously tested. One hypothesis is that a partial agonist stimulates the same reward circuit that nicotine does, albeit weakly, and that this activity would reduce craving. The second hypothesis is that partial agonist therapies work by decreasing the effects of a self-administered full agonist (e.g. nicotine). This second mechanism seems especially likely if the contrasting pharmacokinetic modes are considered, with the therapeutic agent pre-administered at a low dose, producing predesensitization and thereby blunting the peaks of receptor activation that would be produced by the more pulsatile administration of nicotine via cigarette smoking. This latter mechanism might also be applied to the patch form of nicotine replacement therapy, although it remains controversial to what degree receptor desensitization plays a role in nicotine self-administration and dependence [42]. As noted above, one complication to a partial agonist therapy for the treatment of nicotine dependence is that, while a candidate drug may have only weak agonist activity at the target receptors (i.e. brain α4β2* nAChR), a drug like varenicline may have serious side-effects due to activity at other receptor subtypes, such as β4-containing receptors found in the peripheral nervous system [38] and homomeric α7 receptors in the brain [11].

Another potentially important, and yet seldom considered, sequela to partial agonist therapies is that, along with blunting drug reward signals, endogenous cholinergic function is likely to be seriously compromised. While varenicline has been shown to improve smoking cessation outcomes, there have been reports of adverse effects with varenicline [43], including the exacerbation of neuropsychiatric conditions [44-48]. These symptoms are likely to be associated with a functional downregulation of α7-type nAChR receptors in schizophrenia and depression [49, 50] and the effects of varenicline to worsen that condition.

Relationship Between Smoking and Depression:

The high co-morbidity between smoking and depression has been well established in the literature. Estimates of the prevalence of nicotine dependence in patients with major depression range from 50-60%, compared to about 25% in the general population [51]. Furthermore, smokers with a history of major depression are 2-3 times more likely to have failed quit attempts compared to non-depressed smokers [52]. Smoking cessation may also lead to the onset of depressive symptoms in smokers with a history of depression [51].

There is strong support for the hypothesis that the co-morbidity of smoking and depression may relate to an induced imbalance between the activity of homomeric and heteromeric nAChR in the brain. Smoking behavior itself produces increases in α4β2-type receptors relative to α7-type receptors [53-55], and in circuits mediating nicotine reward these receptors can play opposite opposing functions [56]. Additionally, depression is strongly associated with stress and stress-related increases in glucocorticoids [57-59], and chronic elevations in corticoids have been shown to reduce the expression and function of homomeric α7-type receptors in the brain [60-64].

Smoking and Neuropsychiatric Disorders:

It is well documented that the incidence of smoking is very high in neuropsychiatric patients, especially those with schizophrenia or ADHD [65-68]. The incidence of smoking in schizophrenics is 80% compared to 25% in the general population [69]. There is good evidence that a deficiency in α7 nAChR function may be a an underlying cause, or at least an important contributing factor to the etiology of these diseases, and several genetic links have been found between α7-related genes and polymorphisms and schizophrenia [70-80]. These data support the widely-held hypothesis that the smoking behavior in both schizophrenics and ADHD patients is a form of self-medication to make up for deficiencies in α7 receptor function. This hypothesis is further supported by studies of auditory gating in schizophrenics and normal individuals. Auditory gating refers to the process which, in normal individuals, allows there to be progressive decreases in the hippocampal EEG response to presentation of a sound with the repetition of the stimulus. It is common for this gating response to be diminished or absent in schizophrenics. However, smoking normalizes auditory evoked potentials in schizophrenics and has also been reported to improve cognitive function and correct eye tracking deficits [69]. Nicotine is also effective in an animal model for auditory gating deficits [81]. Consistent with the hypothesis that this effect of nicotine is mediated by α7 receptors, impairment in auditory sensory gating has been linked to the α7 nicotinic receptor gene (chromosomal locus15q14) [82, 83] and α7-selective agonists have been shown to reduce the gating deficits in the animal models [67, 84, 85]. Clinical trials are now ongoing and preliminary findings indicate that in human schizophrenics, the α7-selective partial agonist, GTS-21 (DMXB-A), improved clinical ratings of negative symptoms of that are generally resistant to treatment with dopamine antagonist antipsychotic drugs [86].

Compromised α7 nAChR function has also been implicated in substance abuse disorders [65] and, as noted above, ADHD [87, 88]. Nicotinic receptors regulate dopaminergic neurotransmission, which is tied to the brain reward systems that mediate nicotine addiction. Dopaminergic neurotransmission is also the primary target of antipsychotic medications [89, 90]. However, while deficits to α7 receptor function may be tied to neuropsychiatric disorders, α7 receptors are not generally believed to be important for the addicting effects of nicotine. It is also interesting to note that clinically important antipsychotic medications can inhibit the function of α7 nAChR, which may limit their therapeutic effectiveness [91]. Taken together, these findings indicate that while self administration of the non-selective agonist nicotine may have palliative effects in schizophrenia, it locks the patients into a cycle of nicotine use and addiction that brings with it all of the other comorbid effects of smoking. Selective stimulation of α7-receptors would avoid that association. Likewise, protection and stimulation of α7-receptor function during smoking cessation attempts may the replace the self-medication function of smoking.

Therapeutic Alternatives.

Varenicline and GTS-21 have both crossed the threshold into safe use in human trials, so that combination therapy with these two drugs is plausible and may be rapidly moved forward clinically. However, it is not clear that either of these drugs are optimized; additional preclinical studies are warranted. For example, if the α7 activity of varenicline produces neuropsychiatric side effects, then drug development should be targeted toward other cytisine derivatives with reduced effects on α7, such as the recently identified candidate 3-pyro-Cyt [92]. Likewise, since the first publications on GTS-21 [93], many alternative α7-selective full and partial agonists have been identified [94].

Summary:

We think that partial agonists for α4/β2* nAChRs like varenicline are appropriate therapeutics to aid in smoking cessation for smokers without a history of depression or other mental illness, but that for neuropsychiatric patients and individuals at high risk for depression, the off-target effect of decreasing the function of α7 receptors may lead to side effects and/or noncompliance. The combination of an α7-selective agent, such as GTS-21, with the current therapeutic agent varenicline will be an improved treatment for high risk patients.

All of the co-morbid health-related effects of smoking will be most effectively avoided by successful smoking cessation. While smoking is declining in the normal population, it remains very high in the neuropsychiatric patient population, suggesting that their needs for the psychoactive effects of nicotine are greater and inadequately met by the current cessation therapies. It is likely that the combination therapies to be tested in this proposal will be suited to the needs of high risk patients, improving their odds of successful smoking cessation with reduced chance of treatment side effects.

Modulation of nAChR Function with Bath-Applied Agonists:

We have evaluated the effects of bath-applied choline [95] and S 24795 [35] on ACh-evoked α7-mediated responses in brain slices and cytisine and TC-25559 effects on the ACh-evoked responses of the α4β2* heteromeric receptor mediated responses of the LGN (not shown). We have extended this approach to defined receptor subtypes expressed in *Xenopus* oocytes. Experiments were conducted on cells expressing HS α4β2 (α4(2)β2(3)), LS α4β2 (α4(3)β2(2)), or α7 nAChR. After obtaining two baseline control ACh responses (10 μM, 30 μM, and 60 μM for HS α4β2, LS α4β2, and α7 nAChR, respectively, the bath solution was switched to one containing choline, nicotine, cytisine, GTS-21, varenicline, or 3-pyr-cyt. Wide ranges of concentrations were tested, and, in general, there were decreases in subsequent ACh-evoked responses that were dependent on the concentration of the agent applied to the bath. One exception was that α7 responses in the presence of low nanomolar concentrations of GTS-21 were potentiated. More typically, ACh responses were decreased in a concentration-dependent manner, as shown for the modulation of the α4β2 subtypes by nicotine (FIG. 1.1). As shown in FIG. 1.1, the effects of the bath-applied agonist reached a plateau after about 30 minutes, and so the values for the 30-40 time points were averaged for all conditions in order to calculate the concentration-response relationships for each of the drug/receptor pairs. The estimated $10_{50}$ values are given in the table below.

Effects of Prolonged Bath Applications on the Inhibition of ACh-Evoked Responses References, each of which is incorporated herein by reference.

1. Picciotto, M., et al., *Acetylcholine receptors containing the beta2 subunit are involved in the reinforcing properties of nicotine*. Nature, 1998. 391: p. 173-177.
2. Champtiaux, N., et al., *Subunit composition of functional nicotinic receptors in dopaminergic neurons investigated with knock-out mice*. J Neurosci, 2003. 23(21): p. 7820-9.
3. Whiting, P. J. and J. M. Lindstrom, *Purification and characterization of a nicotinic acetylcholine receptor from chick brain*. Biochem, 1986. 25: p. 2082-2093.
4. Seguela, P., et al., *Molecular cloning, functional properties and distribution of rat brain alpha 7: a nicotinic cation channel highly permeable to calcium*. J Neurosci, 1993. 13(2): p. 596-604.
5. DelToro, E. D., et al., *Immunocytochemical localization of the α7 subunit of the nicotinic acetylcholine receptor in the rat central nervous system*. J Comp Neurol, 1994. 349: p. 325-342.
6. Wang, H., et al., *Nicotinic acetylcholine receptor alpha7 subunit is an essential regulator of inflammation*. Nature, 2003. 421(6921): p. 384-8.
7. Lindstrom, J., et al., *Immunochemical tests of acetylcholine receptor subunit models*. Nature, 1984. 311: p. 573-575.
8. Alkondon, M. and E. X. Albuquerque, *Diversity of nicotinic acetylcholine receptors in rat hippocampal neurons. I. Pharmacological and functional evidence for distinct structural subtypes*. J. Pharmacol. Exp. Ther., 1993. 265 (3): p. 1455-1473.
9. Alkondon, M., et al., *Diversity of nicotinic acetylcholine receptors in rat hippocampal neurons. II. The rundown and inward rectification of agonist-elicited whole cell currents and identification of receptor subunits by in situ hybridization*. J. Phamacol. Exp. Ther., 1994. 271: p. 494-506.
10. Alkondon, M. and E. X. Albuquerque, *Diversity of nicotinic acetylcholine receptors in rat hippocampal neurons. III. Agonist actions of the novel alkaloid epibatidine and analysis of type II current*. J. Pharmcol. Exp. Therap., 1995. 274(2): p. 771-782.
11. Papke, R. L. and J. K. P. Papke, *Comparative pharmacology of rat and human alpha7 nAChR conducted with net charge analysis*. Br J of Pharm, 2002. 137(1): p. 49-61.

| | $IC_{50}$ values | | | | | |
|---|---|---|---|---|---|---|
| | choline | nicotine | cytisine | GTS-21 | Varenicline | 3-pyr-cyt |
| HSα4β2 | 100 ± 80 μM | 15 ± 5 nM | 8 ± 5 nM | 170 ± 100 nM | 2.4 ± 1.2 nM | 653 ± 500 nM |
| LSα4β2 | >1 mM | 55 ± 16 nM | 85 ± 44 nM | 1.0 ± 0.4 μM | 2.8 ± 1.2 nM | 5.4 ± 4.0 μM |
| α7 | 6.7 ± 1.2 μM | 1.0 ± 0.4 μM | 300 ± 200 nM | 1.2 ± 0.4 μM* | 334 ± 132 nM | 103 ± 25 μM |

α4β2 receptor ACh-evoked responses reported as peak currents,
α7 responses reported as net charge.
*at concentrations ≤100 nM bath application of GTS-21 produced a potentiation of α7 ACh-evoked currents.

These data allow us to predict the degree to which the various receptor subtypes will be inhibited by therapeutic presence of specific ligands. Interestingly, the LS form of α4β2 receptors were significantly less sensitive than HS α4β2 receptors to all of the ligands tested except varenicline. It is notable that the α7 receptor responses were potentiated by GTS-21 at concentrations which had only modest effects on the α4β2 receptor types (FIG. 1.2). This sort of activity may relate to the stabilization of ligand bound nonconducting states which we have previously shown can prime the α7 receptor for the potentiating effects of the allosteric modulator PNU-120596.

12. Gopalakrishnan, M., et al., *Stable expression and pharmacological properties of the human α7 nicotinic acetylcholine receptor*. Eur. J. Pharm., 1995. 290: p. 237-246.
13. Uteshev, V. V., E. M. Meyer, and R. L. Papke, *Activation and inhibition of native neuronal alpha-bungarotoxin-sensitive nicotinic ACh receptors*. Brain Res, 2002. 948(1-2): p. 33-46.
14. Liu, Q., et al., *A novel nicotinic acetylcholine receptor subtype in basal forebrain cholinergic neurons with high sensitivity to amyloid peptides*. J Neurosci, 2009. 29(4): p. 918-29.

15. Nelson, M. E., et al., *Alternate stoichiometries of alpha4beta2 nicotinic acetylcholine receptors*. Mol Pharmacol, 2003. 63(2): p. 332-41.
16. Collins, A. C., et al., *The road to discovery of neuronal nicotinic cholinergic receptor subtypes*. Handb Exp Pharmacol, 2009(192): p. 85-112.
17. Zhou, Y., et al., *Human alpha4beta2 acetylcholine receptors formed from linked subunits*. J Neurosci, 2003. 23(27): p. 9004-15.
18. Albuquerque, E. X., et al., *Properties of neuronal nicotinic acetylcholine receptors: Parmacological characterization and modulation of synaptic function*. J. Pharmacol. Exp. Ther., 1997. 280: p. 1117-1136.
19. Role, L. and D. Berg, *Nicotinic receptors in the development and modulation of CNS synapses*. Neuron, 1996. 16(6): p. 1077-1085.
20. Wonnacott, S., et al., *Presynaptic modulation of transmitter release by nicotinic receptors*. Prog Brain Res, 1989. 79: p. 157-63.
21. Ji, D., R. Lape, and J. A. Dani, *Timing and location of nicotinic activity enhances or depresses hippocampal synaptic plasticity*. Neuron, 2001. 31(1): p. 131-41.
22. Radcliffe, K. A., et al., *Nicotinic modulation of glutamate and GABA synaptic transmission of hippocampal neurons*. Ann N Y Acad Sci, 1999. 868: p. 591-610.
23. Buhler, A. V. and T. V. Dunwiddie, *alpha7 nicotinic acetylcholine receptors on GABAergic interneurons evoke dendritic and somatic inhibition of hippocampal neurons*. J Neurophysiol, 2002. 87(1): p. 548-57.
24. Thinschmidt, J. S., et al., *Septal innervation regulates the function of alpha7 nicotinic receptors in CA1 hippocampal interneurons*. Exp Neurol, 2005. 195(2): p. 342-52.
25. Frazier, C. J., B. W. Strowbridge, and R. L. Papke, *Nicotinic acetylcholine receptors on local circuit neurons in the dentate gyrus: a potential role in the regulation of granule cell excitability*. J Neurophysiol, 2003. 89(6): p. 3018-3028.
26. Roth, A. L., R. D. Shoop, and D. K. Berg, *Targeting alpha7-containing nicotinic receptors on neurons to distal locations*. Eur J Pharmacol, 2000. 393(1-3): p. 105-12.
27. Descarries, L., V. Gisiger, and M. Steriade, *Diffuse transmission by acetylcholine in the CNS*. Prog Neurobiol, 1997. 53(5): p. 603-25.
28. Rahman, S., et al., *Neuronal nicotinic receptors as brain targets for pharmacotherapy of drug addiction*. CNS Neurol Disord Drug Targets, 2008. 7(5): p. 422-41.
29. Rose, J. E., F. M. Behm, and E. C. Westman, *Nicotine-mecamylamine treatment for smoking cessation: the role of pre-cessation therapy*. Exp. Clin. Psychopharmacol., 1998. 6(3): p. 331-43.
30. Dwoskin, L. P., et al., *Subtype-selective nicotinic receptor antagonists: potential as tobacco use cessation agents*. Bioorg Med Chem Lett, 2004. 14(8): p. 1863-7.
31. Lee, M. G., et al., *Cholinergic basal forebrain neurons burst with theta during waking and paradoxical sleep*. J Neurosci, 2005. 25(17): p. 4365-9.
32. Hasselmo, M. E., *The role of acetylcholine in learning and memory*. Curr Opin Neurobiol, 2006. 16(6): p. 710-5.
33. Marrosu, F., et al., *Microdialysis measurement of cortical and hippocampal acetylcholine release during sleep-wake cycle in freely moving cats*. Brain Res, 1995. 671(2): p. 329-32.
34. Rose, J. E., et al., *Arterial nicotine kinetics during cigarette smoking and intravenous nicotine administration: implications for addiction*. Drug Alcohol Depend, 1999. 56(2): p. 99-107.
35. Lopez-Hernandez, G., et al., *Partial agonist and neuromodulatory activity of S 24795 for alpha7 nAChR responses of hippocampal interneurons*. Neuropharmacology, 2007. 53(1): p. 134-44.
36. Kuryatov, A., et al., *Nicotine acts as a pharmacological chaperone to up-regulate human alpha4beta2 acetylcholine receptors*. Mol Pharmacol, 2005. 68(6): p. 1839-51.
37. Etter, J. F., et al., *Cytisine for smoking cessation: a research agenda*. Drug Alcohol Depend, 2008. 92(1-3): p. 3-8.
38. Papke, R. L. and S. F. Heinemann, *The partial agonist properties of cytisine on neuronal nicotinic receptors containing the beta2 subunit*. Mol. Pharm., 1994. 45: p. 142-149.
39. Pabreza, L. A., S. Dhawan, and K. J. Kellar, *[$^3H$]Cytisine binding to nicotinic cholinergic receptors in brain*. Mol Pharm, 1991. 39: p. 9-12.
40. Etter, J. F., *Cytisine for smoking cessation: a literature review and a meta-analysis*. Arch Intern Med, 2006. 166 (15): p. 1553-9.
41. Mihalak, K. B., F. I. Carroll, and C. W. Luetje, *Varenicline is a partial agonist at alpha4beta2 and a full agonist at alpha7 neuronal nicotinic receptors*. Mol Pharmacol, 2006. 70(3): p. 801-5.
42. Picciotto, M. R., et al., *It is not "either/or": activation and desensitization of nicotinic acetylcholine receptors both contribute to behaviors related to nicotine addiction and mood*. Prog Neurobiol, 2008. 84(4): p. 329-42.
43. Freedman, R., *Exacerbation of schizophrenia by varenicline*. Am J Psychiatry, 2007. 164(8): p. 1269.
44. McClure, J. B., et al., *Mood, Side-effects and Smoking Outcomes Among Persons With and Without Probable Lifetime Depression Taking Varenicline*. J Gen Intern Med, 2009.
45. Philip, N. S., et al., *Varenicline augmentation in depressed smokers: an 8-week, open-label study*. J Clin Psychiatry, 2009.
46. Lyon, G. J., *Possible varenicline-induced paranoia and irritability in a patient with major depressive disorder, borderline personality disorder, and methamphetamine abuse in remission*. J Clin Psychopharmacol, 2008. 28(6): p. 720-1.
47. Pirmoradi, P., S. Roshan, and S. S, Nadeem, *Neuropsychiatric disturbance after initiation of varenicline in a patient with a history of alcohol abuse and major depression*. Am J Health Syst Pharm, 2008. 65(17): p. 1624-6.
48. Pumariega, A. J., R. Nelson, and L. Rotenberg, *Varenicline-induced mixed mood and psychotic episode in a patient with a past history of depression*. CNS Spectr, 2008. 13(6): p. 511-4.
49. Sparks, J. A. and J. R. Pauly, *Effects of continuous oral nicotine administration on brain nicotinic receptors and responsiveness to nicotine in C57Bl/6 mice*. Psychopharmacology (Berl), 1999. 141(2): p. 145-53.
50. Rasmussen, B. A. and D. C. Perry, *An autoradiographic analysis of [125I]alpha-bungarotoxin binding in rat brain after chronic nicotine exposure*. Neurosci Lett, 2006. 404 (1-2): p. 9-14.
51. Glassman, A. H., et al., *Smoking, smoking cessation, and major depression*. JAMA, 1990. 264(12): p. 1546-9.
52. Covey, L. S., A. H. Glassman, and F. Stetner, *Cigarette smoking and major depression*. J Addict Dis, 1998. 17(1): p. 35-46.
53. Lester, H. A., et al., *Nicotine is a selective pharmacological chaperone of acetylcholine receptor number and stoichiometry. Implications for drug discovery*. AAPS J, 2009. 11(1): p. 167-77.

54. Gentry, C. L. and R. J. Lukas, *Regulation of nicotinic acetylcholine receptor numbers and function by chronic nicotine exposure.* Curr Drug Targets CNS Neurol Disord, 2002. 1(4): p. 359-85.
55. Mousavi, M., et al., *Protein and mRNA levels of nicotinic receptors in brain of tobacco using controls and patients with Alzheimer's disease.* Neuroscience, 2003. 122(2): p. 515-20.
56. Mansvelder, H. D., J. R. Keath, and D. S. McGehee, *Synaptic mechanisms underlie nicotine-induced excitability of brain reward areas.* Neuron, 2002. 33(6): p. 905-19.
57. Pittenger, C. and R. S. Duman, *Stress, depression, and neuroplasticity: a convergence of mechanisms.* Neuropsychopharmacology, 2008. 33(1): p. 88-109.
58. Krishnan, V. and E. J. Nestler, *The molecular neurobiology of depression.* Nature, 2008. 455(7215): p. 894-902.
59. Johnson, S. A., N. M. Fournier, and L. E. Kalynchuk, *Effect of different doses of corticosterone on depression-like behavior and HPA axis responses to a novel stressor.* Behav Brain Res, 2006. 168(2): p. 280-8.
60. Bullock, A. E., et al., *Neurosteroids modulate nicotinic receptor function in mouse striatal and thalamic synaptosomes.* J Neurochem, 1997. 68(6): p. 2412-23.
61. Stitzel, J. A., D. A. Farnham, and A. C. Collins, *Chronic corticosterone treatment elicits dose-dependent changes in mouse brain alpha-bungarotoxin binding.* Neuroscience, 1996. 72(3): p. 791-9.
62. Robinson, S. F., et al., *Changes in sensitivity to nicotine and brain nicotinic receptors following chronic nicotine and corticosterone treatments in mice.* Pharmacol Biochem Behav, 1996. 54(3): p. 587-93.
63. Grun, E. U., et al., *Corticosterone reversibly alters brain alpha-bungarotoxin binding and nicotine sensitivity.* Pharmacol Biochem Behav, 1995. 52(3): p. 629-35.
64. Pauly, J. R. and A. C. Collins, *An autoradiographic analysis of alterations in nicotinic cholinergic receptors following 1 week of corticosterone supplementation.* Neuroendocrinology, 1993. 57(2): p. 262-71.
65. Benowitz, N. L., *Pharmacology of nicotine: addiction, smoking-induced disease, and therapeutics.* Annu Rev Pharmacol Toxicol, 2009. 49: p. 57-71.
66. Levin, E. D. and A. H. Rezvani, *Nicotinic interactions with antipsychotic drugs, models of schizophrenia and impacts on cognitive function.* Biochem Pharmacol, 2007. 74(8): p. 1182-91.
67. Olincy, A. and K. E. Stevens, *Treating schizophrenia symptoms with an alpha7 nicotinic agonist, from mice to men.* Biochem Pharmacol, 2007. 74(8): p. 1192-201.
68. Wilens, T. E., et al., *Cigarette smoking associated with attention deficit hyperactivity disorder.* J Pediatr, 2008. 153(3): p. 414-9.
69. Leonard, S., S. Mexal, and R. Freedman, *Smoking, Genetics and Schizophrenia: Evidence for Self Medication.* J Dual Diagn, 2007. 3(3-4): p. 43-59.
70. Deutsch, S. I., et al., *Therapeutic implications of a selective alpha7 nicotinic receptor abnormality in schizophrenia.* Isr J Psychiatry Relat Sci, 2005. 42(1): p. 33-44.
71. Freedman, R., C. E. Adams, and S. Leonard, *The alpha7-nicotinic acetylcholine receptor and the pathology of hippocampal interneurons in schizophrenia.* J. Chem. Neuroanat., 2000. 20(3-4): p. 299-306.
72. Gault, J., et al., *Comparison of polymorphisms in the alpha7 nicotinic receptor gene and its partial duplication in schizophrenic and control subjects.* Am J Med Genet B Neuropsychiatr Genet, 2003. 123(1): p. 39-49.
73. Guan, Z. Z., et al., *Decreased protein level of nicotinic receptor alpha7 subunit in the frontal cortex from schizophrenic brain.* Neuroreport, 1999. 10(8): p. 1779-82.
74. Kumari, V. and P. Postma, *Nicotine use in schizophrenia: the self medication hypotheses.* Neurosci Biobehav Rev, 2005. 29(6): p. 1021-34.
75. Leonard, S., et al., *Nicotinic receptor function in schizophrenia.* Schizophr Bull, 1996. 22(3): p. 431-45.
76. Leonard, S., et al., *Smoking and schizophrenia: abnormal nicotinic receptor expression.* Eur J Pharmacol, 2000. 393 (1-3): p. 237-42.
77. Leonard, S., et al., *Association of promoter variants in the alpha7 nicotinic acetylcholine receptor subunit gene with an inhibitory deficit found in schizophrenia.* Arch Gen Psychiatry, 2002. 59(12): p. 1085-96.
78. Martin, L. F., W. R. Kern, and R. Freedman, *Alpha-7 nicotinic receptor agonists: potential new candidates for the treatment of schizophrenia.* Psychopharmacology (Berl), 2004. 174(1): p. 54-64.
79. Mazurov, A., T. Hauser, and C. H. Miller, *Selective alpha7 nicotinic acetylcholine receptor ligands.* Curr Med Chem, 2006. 13(13): p. 1567-84.
80. Olincy, A., et al., *Proof-of-concept trial of an alpha7 nicotinic agonist in schizophrenia.* Arch Gen Psychiatry, 2006. 63(6): p. 630-8.
81. Stevens, K. E. and K. D. Wear, *Normalizing effects of nicotine and a novel nicotinic agonist on hippocampal auditory gating in two animal models.* Pharmacol Biochem Behav, 1997. 57(4): p. 869-74.
82. Hajos, M. and B. N. Rogers, *Targeting alpha7 Nicotinic Acetylcholine Receptors in the Treatment of Schizophrenia.* Curr Pharm Des, 2009.
83. Martin, L. F. and R. Freedman, *Schizophrenia and the alpha7 nicotinic acetylcholine receptor.* Int Rev Neurobiol, 2007. 78: p. 225-46.
84. Hauser, T. A., et al., *TC-5619: an alpha7 neuronal nicotinic receptor-selective agonist that demonstrates efficacy in animal models of the positive and negative symptoms and cognitive dysfunction of schizophrenia.* Biochem Pharmacol, 2009. 78(7): p. 803-12.
85. O'Neill, H. C., et al., *DMXB, an alpha7 nicotinic agonist, normalizes auditory gating in isolation-reared rats.* Psychopharmacology (Berl), 2003. 169(3-4): p. 332-9. Epub 2003 May 21.
86. Freedman, R., et al., *Initial phase 2 trial of a nicotinic agonist in schizophrenia.* Am J Psychiatry, 2008. 165(8): p. 1040-7.
87. Wilens, T. E. and M. W. Decker, *Neuronal nicotinic receptor agonists for the treatment of attention-deficit/hyperactivity disorder: focus on cognition.* Biochem Pharmacol, 2007. 74(8): p. 1212-23.
88. Gehricke, J. G., et al., *Effects of transdermal nicotine on symptoms, moods, and cardiovascular activity in the everyday lives of smokers and nonsmokers with attention-deficit/hyperactivity disorder.* Psychol Addict Behav, 2009. 23(4): p. 644-55.
89. Zoli, M., et al., *Identification of the nicotinic receptor subtypes expressed on dopaminergic terminals in the rat striatum.* J Neurosci, 2002. 22(20): p. 8785-9.
90. Grady, S. R., et al., *Characterization of nicotinic agonist-induced [(3)H]dopamine release from synaptosomes prepared from four mouse brain regions.* J Pharmacol Exp Ther, 2002. 301(2): p. 651-60.
91. Grinevich, V. P., et al., *Atypical antipsychotics as noncompetitive inhibitors of alpha4beta2 and alpha7 neuronal nicotinic receptors.* Neuropharmacology, 2009.

92. Mineur, Y. S., et al., *Cytisine-based nicotinic partial agonists as novel antidepressant compounds.* J Pharmacol Exp Ther, 2009. 329(1): p. 377-86.

93. de Fiebre, C. M., et al., *Characterization of a family of anabaseine-derived compounds reveals that the 3-(4)-dimethylaminocinnamylidine derivative (DMAC) is a selective agonist at neuronal nicotinic α7/[$^{125}$I]α-bungarotoxin receptor subtypes.* Mol Pharm, 1995. 47: p. 164-171.

94. Papke, R. L., et al., *Activation and desensitization of nicotinic alpha7-type acetylcholine receptors by benzylidene anabaseines and nicotine.* J. P. E. T., 2009. 329(2): p. 791-807.

95. Uteshev, V. V., E. M. Meyer, and R. L. Papke, *Regulation of neuronal function by choline and 4OH-GTS-21 through alpha7 nicotinic receptors.* J Neurophysiol, 2003. 89(4): p. 33-46.

Example 2

Brief Introduction:

Partial agonist therapies rely variously on two hypotheses: that the partial agonists have their effects through chronic low-level receptor activation; or that the partial agonists work by decreasing the effects of endogenous or exogenous full agonists. The relative significance of these activities is likely to depend on whether acute or chronic effects are considered. We studied nAChR expressed in *Xenopus* oocytes, testing a model for the acute interactions between ACh and weak partial agonists. Data were best fit to a basic competition model that included an additional factor for noncompetitive inhibition. Partial agonists effects were compared to the nAChR antagonist bupropion in prolonged bath application experiments that were designed to mimic prolonged drug exposure typical of therapeutic drug delivery. A primary effect of prolonged application of nicotine was to decrease the response of all nAChR subtypes to acute applications of ACh. Additionally, nicotine, cytisine, and varenicline produced detectable steady-state activation of α4β2* ((α4)$_2$(β2)$_3$, (α4)$_3$(β2)$_2$ and (α4)$_2$(β2)$_2$α5)) receptor subtypes that was not seen with other test compounds. Partial agonists produced, no detectable steady-state activation of α7 nAChR, but appeared to show small potentiation of ACh-evoked responses; however, "run-up" of α7 ACh responses was also sometimes observed under control conditions. Potential off-target effects of the partial agonists therefore included the modulation of α7 responses by α4β2 partial agonists, and decreases in α4β2* responses by α7-selective agonists. These data indicate the dual effects expected for α4β2* partial agonists and provide models and insights for utility of partial agonists in therapeutic development.

Introduction:

One important factor limiting the efficacy of nicotinic partial agonist therapies for smoking cessation or other indications is the likelihood of side effects associated with the activation or inhibition of other nAChR subtypes. Both varenicline and cytisine are likely to have such off-target effects since, along with partial agonism of α4β2*-nAChR, they are full agonists for the α3β4*-nAChR of autonomic ganglia and homomeric α7-nAChR found in brain and other tissues (Luetje and Patrick, 1991; Papke and Papke, 2002). The α7-nAChR are also proposed targets for several partial agonist therapies for such diverse indications as Alzheimer's disease, schizophrenia, and inflammatory disease (Kern, 2000; de Jonge and Ulloa, 2007), and α7 partial agonists may have off-target effects as antagonists of other nAChR (de Fiebre et al., 1995).

The natural balance of receptor subtypes may be perturbed in drug-dependent or disease states. There is well-documented up-regulation of α4β2-nAChR in smokers and animals exposed to chronic nicotine (Benowitz, 2009). Concomitant to nicotine dependence there may also be a shift in the predominant form of α4β2-nAChR in the brain from a low sensitivity form (LS α4β2), believed to containing three α4 subunits and two β2 subunits (α4(3)β2(2)), to a high sensitivity form (HS α4β2), with the reverse subunit stoichiometry (α4(2)β2(3)) (Walsh et al., 2008).

While there is upregulation of the targeted receptor for smoking cessation, there is good evidence that there may be functional deficiencies in the targeted α7 receptor in schizophrenia (Leonard et al., 2000). Expression of the α7 receptor is also down-regulated by stress hormones, and decreased α7 receptor function may be associated with depression (Lai et al., 2001). The incidence of smoking is very high in the mentally ill, and nicotine dependence in this patient population may develop secondarily to self-medication with nicotine in compensation for decreased α7-nAChR receptor function (Leonard et al., 2000). Numerous adverse neuropsychiatry effects have been reported for varenicline therapies (McClure et al., 2009), leading the FDA to issue a black-box warning. It may be the case that these adverse effects were due at least in part to off-target effects on α7 receptors in patients already suffering from disease-related decreases in α7 function.

In this Example we present a comprehensive characterization of α4 and α7 partial agonists using defined nAChR receptor subtypes (α4(3)β2(2), (α4(2)β2(3), (α4(2)β2(2)α5 and α7) expressed in *Xenopus* oocytes. We propose and test a quantitative model for the acute buffering effects of α7 and α4β2 partial agonists on the activity of the endogenous full agonist, acetylcholine (ACh). We make an important extension of those studies to place the partial agonist delivery into a context relevant for therapeutics, evaluating how activation by ACh will be perturbed by the chronic applications of the partial agonists for both target and off target receptors.

The predominant effect of bath-applied partial agonists appeared to be predesensitization. However, within limited concentration ranges, nicotine and the α4β2 partial agonists cytisine and varenicline also produced mecamylamine-sensitive steady-state activation. Interestingly, while steady-state activation of α7 receptors was not detected, low concentrations of the α7-selective partial agonists 3-2,4,dimethoxybenzylidene anabaseine (GTS-21) and 2-[2-(4-bromophenyl)-2-oxoethyl]-1-methylpyridinium (S 24795) were seen to potentiate, or prime the receptors for greater activation by ACh pulses. However "run up" of ACh-evoked responses was also seen in some control experiments suggesting that ACh may be self-priming. Such priming activity suggests a novel mechanism of action for α7-selective drugs in therapeutics, and possibly the utility of combination therapies to protect α7 receptor function from the off-target effects of other drugs such as varenicline.

Methods:

Heterologous Expression of nAChR in *Xenopus* Oocytes cDNA: Human nAChR receptor clones and concatamers were obtained from Dr. Jon Lindstrom (University of Pennsylvania, Philadelphia Pa.). The human RIC-3 clone, obtained from Dr. Millet Treinin (Hebrew University, Jerusalem Israel), was co-injected with α7 to improve the levels and speed of receptor expression.

Oocyte preparation: Oocytes were surgically removed from mature *Xenopus laevis* frogs and injected with 50 nl (5-20 ng) of appropriate nAChR subunit cRNAs as described previously (Horenstein et al., 2008).

Oocyte recording and data analysis:

Experiments were conducted using OpusXpress 6000A (Molecular Devices, Union City Calif.) and analyzed as described previously (Papke and Papke, 2002; Horenstein et al., 2008; Papke and Stokes, 2010).

Acute co-application experiments: Following two initial ACh control applications (300 µM for the α7 experiments and 100 µM for the (α4(3)β2(2), experiments) cells were treated in alternation with mixtures of ACh and the partial agonist or ACh alone. Data were rejected if there was more than a 25% variation between the ACh controls prior or subsequent to the experimental co-application. The data used for the fitting procedures were average values from at least 4 cells given the same treatments, normalized to the respective ACh control responses recorded prior to the experimental co-applications. In the case of the α4β2 data, a further correction was made to adjust for the ratio of the ACh control and the ACh maximum response, since responses to the control concentration of ACh were only 46% the amplitude of the ACh maximal responses (see below).

Bath application experiments: Baseline conditions were defined by two ACh control applications made prior to the introduction of the test compounds into the bath. The ACh control concentrations were 30 µM for (α4(3)β2(2), 10 µM for (α4(2)β2(3), 3 µM for α4β2α5 and 60 µM for α7. These concentrations were selected since they gave robust responses that showed little or no rundown when applied repeatedly at four minute intervals. They were determined in separate experiments to be the $EC_{46}$, $EC_{90}$, $EC_{50}$, and $EC_{60}$ for the respective subtypes. Once the experimental solutions were introduced in the bath, cells were repeatedly stimulated at 223 s (α7) or 277 s (non-α7) intervals with ACh at the control concentration made up in the experimental bath solution. All data obtained after the application of test compounds to the bath were normalized relative to the average of the first two ACh controls recorded in regular bath solution. Initial experiments were run for 50 minutes after the introduction of the experimental compounds into the bath. However, since the maximal effects were achieved after only 25 minutes, subsequent bath application experiments were run for only 35 minutes. Data in the summary plots are the average of the data from the last three of these ACh probes.

Modeling of Acute Agonist/Partial Agonist Interactions:

Acute responses to agonist/partial agonist applications were fit with a general non-linear regression model, implemented as an option in a Windows data analyses and graphical presentation program (CAS Data Forge). The terms $n_a$, $n_p$, $n_i$, $R_{max}p$, $In_{max}p$, $EC_{50}a$, $EC_{50}p$, and $IC_{50}p$ were given starting estimates based on the data obtained with the drugs applied separately. Tolerance factor (typically $1\times10^{-5}$) range limits for each parameter were specified. For S 24795, the observed values were represented by a matrix of 11 values of ACh (a) and 10 values of S 24795 (p) for a total of 110 observations, with each value being the mean of multiple measurements for the given a and p concentrations. For cytisine, the replicate values for each ACh (a) and cytisine (p) concentration were used for a total across all cells of 1416 observations. A predicted matrix was then calculated for each cell of the matrix, based on the a and p concentrations, the set of parameters listed above, and the governing equation. The residuals across all cells were calculated, and an iterative process was utilized to revise the parameters to minimize the residuals and allow the estimates to be revised accordingly. When the difference of estimates for any given parameter for consecutive iterations fell below the tolerance factor, that parameter was fixed at the last estimate. When all parameters were fixed or no convergent solution was found, the process stopped, and the set of parameters representing the best fit along with the resulting matrix was provided.

Results:

Modulation of α7 by the Selective Agonist S 24795:

We have previously reported (Lopez-Hernandez et al., 2007) that when the weak α7-selective partial agonist S 24795 was co-applied with ACh to hippocampal interneurons expressing α7 receptors, the co-application responses could be variously increased, decreased, or unchanged, relative to the responses evoked by ACh alone. By comparison of the data obtained from brain slice experiments to data obtained for α7 receptors expressed in *Xenopus* oocytes, under conditions when the actual concentration of the full and partial agonists were known, we were able to estimate the dilution factor of the pressure applications in the hippocampal slice experiments to be about 30-fold. We have extended those experiments of receptors expressed in oocytes to encompass full ranges of mixed concentrations, and have evaluated the data in the context of the model presented in FIG. 2.1. The model is based largely on competitive interactions between the full and partial agonists. However, since it has been suggested that partial agonists may also have limiting inhibitory effects that are noncompetitive (Luetje and Patrick, 1991), we have also included a factor allowing for noncompetitive inhibition.

The competitive activity was modeled as the weighted sum of the response evoked by the full and partial agonists, adjusted for both receptor availability and the effective concentration of the drugs, allowing for separate $EC_{50}$ and n values for the two drugs. The $I_{max}$ for the full agonist was constrained to 1 while the $I_{max}$ for the partial agonist was a free parameter <1.0.

The data shown as points in FIG. 2.2A are the means of the experimental (net charge) data obtained when ACh at concentrations ranging from 30 nM to 1 mM co-applied with S 24795 through the same concentration range. Each point represents the average response of at least four cells normalized to the ACh maximum (net charge) response. Curve fit values for the drugs when applied alone were used as seeds for the competitive interactions. A least squares analysis was then conducted (see Methods), and curves generated by the best fit of the complete model are shown as the lines FIG. 2.2A (parameters of the fit are given in Table 1). For these data, the best fit was achieved with relatively minor weight ascribed to the factor for noncompetitive inhibition (i.e. the curves were not greatly altered if the factor was eliminated). The largest disparities between the observed and predicted values were for the range of high ACh concentration co-applied with relatively low concentrations of S 24795. This is not surprising because with the applications of high ACh concentration the receptor mediated response is generated almost entirely before the solution exchange is complete (Papke and Papke, 2002), so that S 24795 concentrations were low at the time of the responses and the predicted competitive effects of S 24795 could not be achieved.

TABLE 1

Best fit values for FIG. 2.2

| | ACh and S 24795 on α7 | | | ACh and cytisine on α4(3)β2(2) | | |
|---|---|---|---|---|---|---|
| Activation | $R_{max}$ | n | $EC_{50}$ | $R_{max}$ | n | $EC_{50}$ |
| ACh | 1.0 | 1.45 | 37 µM | ACh 1.0 | 1.5 | 148 µM |
| S 24795 | 0.20 | 0.85 | 14 µM | Cytisine 0.35 | 0.61 | 88 µM |
| Inhibition | $In_{max}$ | n | $IC_{50}$ | $In_{max}$ | n | $IC_{50}$ |
| | 1.0 | 0.26 | 1 mM | 0.7 | 1.7 | 32 µM |

Acute Modulation of ACh-Evoked Responses of Low Sensitivity α4(3)β2(2) nAChR by the α4β2 Partial Agonist Cytisine:

We tested effects of cytisine co-application on the ACh-evoked responses of human α4β2 receptors expressed in *Xenopus* oocytes. By using an α4-β2 concatamer co-expressed with monomeric α4 (Zhou et al., 2003), we were able to obtain pure populations of the form of α4β2 believed to be most abundantly expressed in human cell lines (Nelson et al., 2003), containing three α4 and two β2 subunits. The data shown as points in FIG. 2.2B are the means of the experimental (peak current) data obtained when ACh at concentrations ranging from 30 nM to 1 mM was co-applied with cytisine through the same concentration range. Each point represents the average response of at least five cells normalized to the ACh maximum (peak current) response. Curve fit values for the drugs when applied alone were used as seeds for the competitive interactions. A least squares analysis (see Methods) was then conducted using data for all of the replicate measurements, and curves generated by the best fit of the complete model are shown as lines FIG. 2.2B (parameters of the fit are given in Table 1). It is interesting to note that, while for the fit of the α7 data with ACh and S 24795 the inhibitory factor for the partial agonist was relatively minor (the best fit for the S 24795 $IC_{50}$ was 70-fold higher than the $EC_{50}$), for the cytisine/ACh interaction the best fit for the cytisine $IC_{50}$ was three-fold lower than the $EC_{50}$. It is unlikely that the difference in the noncompetitive component's importance for α4β2-nAChR data vs. the α7-nAChR data reflect the properties of the activation of the α7-nAChR, since many α7 partial agonists also manifest strong noncompetitive antagonist activity (Papke et al., 2009).

Modulation of ACh-Evoked Responses of α7 and α4β2 Receptors Expressed in *Xenopus* Oocytes by Bath-Applied Nicotine:

While an acute co-application protocol was appropriate to test the basic model of full and partial agonist competition shown in FIG. 2.1, such a protocol is not readily applicable to either therapeutics or drug self-administration, when drug delivery to the brain is relatively slow and prolonged. Under such circumstances effects of the drugs will pre-equilibrate prior to presentation of phasic stimulations by endogenous ACh. In the case of nicotine self-administration and nicotine replacement therapies, there is controversy about the degree to which chronic low levels of nicotine activate or simply desensitize nAChR in the brain (Picciotto et al., 2008). To address this question, we determined the degree to which nAChR receptor function was able to be modulated by bath-applied nicotine. The results in FIG. 2.3 show that nicotine is a potent agent for producing predesensitization of α4β2* nAChR with relatively little effect on ACh-evoked activation of α7, except at high concentrations.

Modulation of ACh-Evoked Responses of α7 and α4β2 Receptors Expressed in *Xenopus* Oocytes by Partial Agonists Used as Smoking Cessation Drugs:

Drugs which are partial agonists for α4β2* receptors have become important candidates for smoking cessation therapies and alternatives to simple nicotine replacement approaches (i.e. nicotine patches or gum). However, it is unclear to what degree drugs such as cytisine, used as a smoking cessation agent in Europe, or varenicline, a cytisine-related compound which has been approved as a smoking cessation aid in both the US and abroad, really differ from nicotine in their modulation of brain nAChR ACh-mediated activity. Therefore, we investigated the ability of these two agents to decrease the ACh-evoked responses of both the high sensitivity (α4(2)β(3)) and low sensitivity (α4(3)β2(2)) forms of human α4β2-nAChR and compared these effects with their ability to modulate the function of α7 nAChR. In acute application experiments both of these agents were strong activators of α7, and in a therapeutic context effects on α7 receptor function would most likely be a negative and certainly considered "off target".

As shown in FIG. 2.4, when bath-applied, within 30 minutes both of these compounds produced progressive concentration-dependent decreases of α4β2 ACh-evoked responses. In order to summarize these data, we calculated the average of the ACh responses obtained after 30±4 minutes of bath application relative to the pretreatment control responses. The lower plots in FIG. 2.4 show those data as a function of the bath concentrations applied and were used to calculate the $IC_{50}$ values in Table 2.

TABLE 2

| | $IC_{50}$ values (nM) for the inhibition of ACh evoked responses by bath applications of agonists and partial agonists | | | |
|---|---|---|---|---|
| | α4(3)β2(2) | α4(2)β2(3) | α4(2)β2(2)α5 | α7 |
| Nicotine | 56 ± 16 | 15 ± 5 | 17 ± 7 | 1,000 ± 380 |
| Cytisine | 27 ± 14 | 8 ± 5 | 3.2 ± 1.6 | 1,200 ± 570 |
| Varenicline | 2.8 ± 1.3 | 1.6 ± 0.5 | 3.3 ± 0.9 | 334 ± 140 |
| 3-pyr-Cyt | 16,000 ± 12000 | 600 ± 500 | 2,300 ± 1,000 | NA |
| GTS-21 | 1,000 ± 400 | 170 ± 100 | | 1,300 ± 475* |
| S 24795 | 36,000 ± 7,000 | 53,000 ± 6,000 | | 15,000 ± 4,000* |

*Inhibition following a phase of potentiation.

Note that varenicline was more potent than cytisine at decreasing α4β2 ACh-evoked responses, and (α4(2)β2(3)) receptors appeared somewhat more sensitive than (α4(3)β2(2)) receptors, although the differences were not statistically significant. The ACh-evoked responses of human α7 receptors were also decreased by the bath applications of these drugs at higher concentrations.

Modulation of ACh-Evoked Responses of α4β2α5 Receptors Expressed in *Xenopus* Oocytes by Bath-Applied Nicotine or Cytisine-Related Compounds:

Recently, attention has been drawn to α5 as a member of a gene cluster associated with high risk for cancer and heavy smoking (Saccone et al., 2007). In the periphery, α5 is most likely expressed in association with the other members of its gene cluster, α3 and β4. In the brain, α5 may be associated with α4 and β2, generating another high sensitivity receptor subtype that could be related to nicotine dependence or reward (Grady et al., 2010). We therefore investigated the effects of bath-applied nicotine, cytisine, and varenicline on α4β2α5 receptors formed by co-expressed α5 with the β2-6-α4 concatamer (Kuryatov et al., 2008). It has been previously reported that such α4β2α5 receptors also show relatively high sensitivity to a variety of agonists (Kuryatov et al., 2008). In our experiments the $EC_{50}$ values of a4β2α5 responses to nicotine, cytisine, and varenicline were 180±20, 18±9, and 35±3 nM, respectively (data not shown). The efficacy of nicotine for α4β2α5 receptors was approximately 35% that of ACh, while cytisine and varenicline had efficacies of 6±1 and 9±1% that of ACh, respectively. In bath application experiments the sensitivity of α4β2α5 nAChR was similar to that of the α4(3)β2(2) and α4(2)β2(3) receptors for all of the agents tested (FIG. 2.5, Table 2).

Steady-State Activation of α4β2* Receptors:

One conundrum related to the therapeutic applications of partial agonists is the question of whether the drugs themselves will produce significant amounts of receptor activation or merely function as time-averaged antagonists of the endogenous activators. Most of the data obtained with the α4β2*-nAChR would support the latter hypothesis (Picciotto et al., 2008). However, it has been proposed that, even when the predominant effect is to induce desensitization, there may nonetheless be sufficient equilibration between activation and desensitization to produce something equivalent to low levels of steady-state activation within a narrow range (window) of drug concentration. Such window currents have been described for the relatively slow desensitizing β4*-nAChR of neurons in the medial habenula (Lester, 2004).

In our bath application experiments we frequently saw small responses at the beginning of the bath applications, and sometimes there were significant shifts in baseline holding current that occurred over the long periods of recording. While increases in baseline current would be consistent with the stimulation of steady-state currents, baseline shifts can occur for other reasons as well, especially if the quality of the voltage clamp diminished over a long period of recording. Therefore we repeated the experiments with the drug-receptor combinations that appeared to have possible increases in steady-state (baseline) current, substituting the ACh probe application 30 minutes after the start of the bath application with a 100 μM pulse of mecamylamine, to definitively test whether there was a receptor-mediated steady-state current contributing to the change in baseline.

A representative experiment is shown in FIG. 2.6. The peak current associated with the bath application of 1 μM varenicline to the α4β2α5 receptors was small compared to the initial 3 μM ACh-evoked response; however, the current was sustained. Even after just 30 minutes of continual bath application, a large shift in baseline was apparent. At that time the cells showed 100% inhibition of transient ACh-evoked responses, and the application of 100 μM mecamylamine caused a return to the original baseline. In this experiment the magnitude of the mecamylamine-sensitive steady-state current was 2.5±5% that of the maximum peak transient current that could be activated by ACh. Table 3 provides a summary of the mecamylamine-sensitive steady-state currents measured for each of the drug-receptor combinations associated with drifting baselines. The greatest steady-state current observed was with α4(2)β2(3) receptors in the presence of 300 nM nicotine. There were no baseline shifts or steady-state currents in α7-expressing cells under any of the drug conditions.

TABLE 3

Mecamylamine-sensitive steady-state activation of α4β2* nAChR, relative to ACh maximum evoked transient responses recorded in oocytes.

|  | α4(3)β2(2) | α4(2)β2(3) | α4(2)β2(2)α5 |
| --- | --- | --- | --- |
| Nicotine | 1.8 ± 0.1% (300 nM) | 7 ± 1% (300 nM) | 2.5 ± 1% (100 nM) |
| Cytisine | 1.1 ± 0.2% (300 nM) | 1.4 ± 0.1% (100 nM) | 2.5 ± 0.5% (1 μM) |
| Varenicline | 1.7 ± 0.2% (1 μM) | 2.1 ± 0.4% (30 nM) | 2.5 ± 0.5% (100 nM) |

Modulation of ACh-Evoked Responses by the Alternative Smoking Cessation Drug Bupropion:

In addition to nicotine replacement and partial agonist therapies, the antidepressant bupropion has been used to improve smoking cessation efforts (Hurt et al., 1997). The basis of this therapeutic approach has been suggested, at least in part, to relate to bupropion's activity as an nAChR antagonist (Slemmer et al., 2000). We applied bupropion to α4-containing nAChR (i.e. α4(3)β2(2), α4(2)β2(3) and α4(2)β2(2)α5) and α7 nAChR at concentrations from 300 nM to 300 μM and saw no activation above our level of detection (not shown). We applied two approaches for measuring the antagonist activity of bupropion: co-applications and prolonged bath application. As shown in FIG. 2.7A, when bupropion was co-applied with control concentrations of ACh (see Methods), all the nAChR subtypes tested were inhibited in a dose-dependent manner. The most potent inhibition was for the α4(3)β2(2) receptors (Table 4). We also tested bupropion with the same bath-application protocol used for the evaluation of the partial agonists. Shown in FIG. 7B are the averages of three ACh-evoked responses after bupropion had been present in the bath for 30 minutes. While the potency of bupropion for the inhibition of α7 and α4(3)β2(2) receptors was relatively unchanged with this protocol (Table 4), the α4(2)β2(3) and α4β2α5 receptors showed partial blockade at relatively low bath concentrations of bupropion, resulting in an inhibition curve with a very low Hill slope. This may have been due to slow equilibration of inhibition for these subtypes, or alternatively might represent multiple mechanisms of inhibition. While these experiments support the potential mechanism of bupropion as an nAChR antagonist, they also indicate a much lower potency for this effect than was seen with nicotine, varenicline, or cytisine (Table 2).

TABLE 4

Inhibition of α7 and α4-containing receptors by bupropion.

| | Co-application | | Bath application | |
|---|---|---|---|---|
| | n | IC$_{50}$ | n | IC$_{50}$ |
| α7 | −0.74 ± 0.09 | 46 ± 7 μM | −1.5 ± 0.5 | 16 ± 3 μM |
| α4(3)β2(2) | −0.93 ± 0.11 | 8.3 ± 1.2 μM | −1.2 ± 0.4 | 5.9 ± 1.5 μM |
| α4(2)β2(3) | −0.80 ± 0.05 | 72 ± 5 μM | −0.40 ± 0.10 | 4.4 ± 2.3 μM |
| α4β2α5 | −0.70 ± 0.04 | 23 ± 2 | −0.47 ± 0.09 | 2.8 ± 1.0 μM |

Modulation of ACh-Evoked Responses by a Novel Cytisine Related Drug:

The success of varenicline, albeit modest, as a smoking cessation agent has led to the development of additional cytisine analogs for smoking cessation and potentially therapeutic agents for treating depression. One such compound is 3-(pyridin-3'-yl)-cytisine (3-pyr-Cyt), an agent proposed to have very little likelihood of off-target α7 activity (Mineur et al., 2009). As shown in FIG. 2.8, 3-pyr-Cyt can decrease the ACh-evoked responses of α4β2 receptors, producing partial inhibition of the α4(2)β2(3) form even at relatively low (30 nM) concentration, although high concentrations are required to achieve strong inhibition (Table 3). Significant inhibition of α7-mediated responses was only achieved with 100 μM, the highest concentration tested. There were no baseline shifts or steady-state currents in the presence of 3-pyr-Cyt. Modulation of ACh-Evoked Responses of α7 and α4β2* Receptors Expressed in *Xenopus* Oocytes by Bath-Application of α7-Selective Compounds:

While α4β2 partial agonists are being developed for smoking cessation and possibly depression, α7-selective partial agonists have been proposed as therapeutics for a wide range of indications from Alzheimer's disease to arthritis (Kem, 2000; de Jonge and Ulloa, 2007). For such drugs, strong inhibition of α4β2* receptors might be considered an undesirable off-target activity. Therefore we investigated the modulation of α4(2)β2(3) and α4(3)β2(2) receptors and α7 by bath applications of the prototypical α7-selective partial agonist GTS-21 (also called DMXBA or diMeOBA). The results shown in FIG. 2.9 indicate that, somewhat unexpectedly, while the responses of α4β2 receptors were decreased in the presence of bath-applied GTS-21, α7 ACh-evoked responses showed significant (p<0.05) potentiation at concentrations (1-100 nM) lower than those which would normally be used to produce transient receptor activation (EC$_{50}$≈6 μM (Papke and Papke, 2002)). The efficacy of GTS-21 for human α7 receptors is relatively low, only about 20% that of ACh, while the responses recorded with bath applications of 30 nM GTS-21 were 37±15% above the baseline controls. We tested whether similar effects might be seen with the alternative low efficacy α7-selective partial agonist S 24795 (FIG. 2.10). These results suggest that low concentrations of an α7-activating drug might have potentiating or priming effects, however similar run-up was also sometimes (although not consistently) observed in control experiments with just repeated applications of ACh to α7-expressing cells (not shown). The washing in and out of ACh in the control experiments might have had a priming effect, similar to that of low concentrations of GTS-21 or S 24795 or alternatively, run-up of α7 responses with repeated stimulations might be a property of the oocyte expression system.

Discussion:

Our experiments with acute co-applications of partial agonists with ACh largely support the traditional view that the combined effects of the drugs can be predicted based on competitive interactions. However, for specific drug-receptor combinations additional factors may be limiting, as was the case with cytisine, which appeared to have additional non-competitive antagonist activity. For other drug-receptor combinations, such as GTS-21 and α7 receptors, at high partial agonist concentrations the induction of stable desensitization will also be a limiting factor (Papke et al., 2009). While the induction of stable desensitization appears to be a factor limiting the efficacy of GTS-21 in acute applications, it does not appear to be an important factor in defining the activity profile of other benzylidene anabaseines or S 24795 (Lopez-Hernandez et al., 2007).

Responses measured in the acute application experiments result from the simultaneous integration of the activation and desensitization produced the drugs in combination. On the time scale of the oocyte experiments, the peak currents are likely to represent the net result of the convolution of these processes and solution exchange (Papke, 2009). In contrast, the bath application experiments allowed for the effects of the partial agonists to approach equilibrium, so that the applications of the full agonist served as a probe of the pre-desensitization endpoints. For the α4-containing receptors used in these studies we were also able to detect and measure steady-state activations that for cytisine and varenicline were rather high, considering the apparently low efficacy of these compounds in acute application experiments.

In the search for candidate drugs to treat nicotine dependence, of equal importance to understanding the functional properties of the specific nAChR in the brain responsible for addiction and dependence is an understanding how the candidate drugs function to either blunt or substitute for the nicotine reward. The concept that an α4β2 partial agonist would have utility as a smoking cessation agent has relied variously on two hypotheses that have not previously been rigorously tested. One hypothesis was that a partial agonist stimulates the same reward circuit that nicotine does, albeit weakly, and that this activity would reduce craving. The second hypothesis is that partial agonist therapies work by decreasing the effects of a self-administered full agonist (e.g., nicotine). This second mechanism seems especially likely if the contrasting pharmacokinetic modes are considered, with the therapeutic agent pre-administered at a low dose, producing predesensitization and thereby blunting the peaks of receptor activation that would be produced by the more pulsatile administration of nicotine via cigarette smoking. This latter mechanism might also be applied to the patch form of nicotine replacement therapy, although it remains controversial to what degree receptor desensitization plays a role in nicotine self-administration and dependence (Picciotto et al., 2008). Our data support the concept that partial agonist therapies may rely on both these mechanisms, although the concentration window for tonic activation appeared to be rather narrow. The in vitro effects we observed occur on physiologically relevant time scales and within concentration ranges for nicotine self-administration and smoking cessation-related therapeutics and are consistent with recent in vivo studies (Marks et al.).

Our data support the plausibility of the hypothesis that at least part of the utility of bupropion as a smoking cessation agent may be due to blockade of nicotine's reinforcing effects mediated by α4* receptors (Slemmer et al., 2000). However, this activity alone would not be equivalent to the effects of a nicotine patch or a partial agonist, since it would not provide a similar factor of tonic activation. Perhaps bupropion's activity as a blocker of dopamine reuptake (Miller et al., 2002) compensates for a decrease in nicotine-mediated dopamine-dependent reward.

In addition to working through these expected competitive mechanisms, our data also support an earlier report which suggested that cytisine may antagonize the function of α4β2 receptors through noncompetitive effects (Luetje and Patrick, 1991). This result is of particular interest since there have been several recent studies suggesting that nicotinic antagonists may have efficacy as antidepressants (Mineur and Picciotto, 2009). It has been shown that in the mouse forced-swim model cytisine is equipotent as the pure antagonist mecamylamine at reducing immobility (Mineur et al., 2009).

Although our data did not indicate that weak α7-selective partial agonists will produce tonic activation of the receptors when present for long periods of time, we observed that under such conditions they did not desensitize and may even potentiate ACh-evoked responses. It may be the case that partial or intermittent occupancy of the α7 binding sites has priming effects for subsequent stimulation, although allosteric modulation based on binding to other sites cannot be ruled out by the available data. However, it has also been proposed that high levels of agonist site occupancy by a strong agonist is intrinsically desensitizing for α7 receptors (Papke et al., 2000). Additionally, although the steady-state applications of α7 agonists at low concentrations did not appear to lessen the acute activation by ACh, it is possible that they could have perturbed the equilibrium among the various ligand-bound non-conducting states, such as those which are competent for activation by allosteric modulators (Papke et al., 2009).

As noted above, one complication to a partial agonist therapy for the treatment of nicotine dependence is that, while a candidate drug may have only weak agonist activity at the target receptors (i.e. brain α4β2* nAChR), a drug like varenicline may have serious side effects due to activity at other receptor subtypes, such as α3β4*-nAChR found in the peripheral nervous system (Papke and Heinemann, 1994) and homomeric α7 receptors in the brain (Papke and Papke, 2002). Therefore it must be considered that an important sequela to nicotinic partial agonist therapies is that, along with blunting drug reward signals, endogenous cholinergic function is likely to be seriously compromised for both on-target and off-target nAChR. While varenicline has been shown to improve smoking cessation outcomes, there have been reports of adverse effects with varenicline, including the exacerbation of neuropsychiatric conditions (McClure et al., 2009). These symptoms are likely to be associated with a functional down-regulation of α7-type nAChR receptors in schizophrenia and depression (Leonard et al., 2000) and the effects of varenicline to worsen that condition.

There is strong support for the hypothesis that the co-morbidity of smoking and depression may relate to an induced imbalance between the activity of homomeric and heteromeric nAChR in the brain (Mineur and Picciotto, 2009). Smoking behavior itself produces increases in α4β2-type receptors relative to α7-type receptors (Lester et al., 2009), and in circuits mediating nicotine reward these receptors can play opposing functions (Mansvelder et al., 2002). Additionally, depression is strongly associated with stress and stress-related increases in glucocorticoids (Pittenger and Duman, 2008), and chronic elevations in corticoids have been shown to reduce the expression and function of homomeric α7-type receptors in the brain (Bullock et al., 1997).

It is well documented that the incidence of smoking is very high in neuropsychiatric patients, especially those with schizophrenia or ADHD (Benowitz, 2009). The incidence of smoking in schizophrenics is 80% compared to 25% in the general population (Leonard et al., 2007). There is good evidence that a deficiency in α7 nAChR function may be an underlying cause, or at least an important contributing factor to the etiology of these diseases, and several genetic links have been found between α7-related genes and polymorphisms and schizophrenia (Olincy et al., 2006). These data support the widely held hypothesis that the smoking behavior in both schizophrenics and ADHD patients is a form of self-medication to make up for deficiencies in α7 receptor function. This hypothesis is further supported by studies of auditory gating in schizophrenics and normal individuals. Consistent with the hypothesis that this effect of nicotine is mediated by α7 receptors, impairment in auditory sensory gating has been linked to the α7 nicotinic receptor gene (chromosomal locus15q14) (Martin and Freedman, 2007), and α7-selective agonists have been shown to reduce the gating deficits in the animal models (Olincy and Stevens, 2007).

Varenicline and GTS-21 have both crossed the threshold into safe use in human trials, so that combination therapy with these two drugs is plausible. However, it is not clear that either of these drugs are optimized; additional preclinical studies are warranted. For example, if the α7 activity of varenicline produces neuropsychiatric side effects, then drug development should be targeted toward other cytisine derivatives with reduced effects on α7, such as the recently identified candidate 3-pyr-Cyt (Mineur et al., 2009). Likewise, since the first publications on GTS-21 (de Fiebre et al., 1995), many alternative α7-selective full and partial agonists such as S 24795 have been identified (Papke et al., 2009). The successful development of such drug candidates into useful therapeutics will benefit the use of protocols such as those described in this work for the detection of both on-target and off-target activities.

References, each of which is incorporated herein by reference

Benowitz N L (2009) Pharmacology of nicotine: addiction, smoking-induced disease, and therapeutics. *Annu Rev Pharmacol Toxicol* 49:57-71.

Bullock A E, Clark A L, Grady S R, Robinson S F, Slobe B S, Marks M J and Collins A C (1997) Neurosteroids modulate nicotinic receptor function in mouse striatal and thalamic synaptosomes. *J Neurochem* 68:2412-2423.

Champtiaux N, Gotti C, Cordero-Erausquin M, David D J, Przybylski C, Lena C, Clementi F, Moretti M, Rossi F M, Le Novere N, McIntosh J M, Gardier A M and Changeux J P (2003) Subunit composition of functional nicotinic receptors in dopaminergic neurons investigated with knock-out mice. *J Neurosci* 23:7820-7829.

de Fiebre C M, Meyer E M, Zoltewicz J, Henry J C, Muraskin S, Kern W R and Papke R L (1995) Characterization of a family of anabaseine-derived compounds reveals that the 3-(4)-dimethylaminocinnamylidine derivative (DMAC) is a selective agonist at neuronal nicotinic α7/[$^{125}$I] α-bungarotoxin receptor subtypes. *Mol Pharm* 47:164-171.

de Jonge W J and Ulloa L (2007) The alpha7 nicotinic acetylcholine receptor as a pharmacological target for inflammation. *Br J Pharmacol* 151:915-929.

Grady S R, Salminen O, McIntosh J M, Marks M J and Collins A C (2010) Mouse striatal dopamine nerve terminals express alpha4alpha5beta2 and two stoichiometric forms of alpha4beta2*-nicotinic acetylcholine receptors. *J Mol Neurosci* 40:91-95.

Horenstein N A, Leonik F M and Papke R L (2008) Multiple pharmacophores for the selective activation of nicotinic alpha7-type acetylcholine receptors. *Mol Pharmacol* 74:1496-1511.

Hurt R D, Sachs D P, Glover E D, Offord K P, Johnston J A, Dale L C, Khayrallah M A, Schroeder D R, Glover P N, Sullivan C R, Croghan I T and Sullivan P M (1997) A comparison of sustained-release bupropion and placebo for smoking cessation. *N Engl J Med* 337:1195-1202.

Kem W R (2000) The brain alpha7 nicotinic receptor may be an important therapeutic target for the treatment of Alzheimer's disease: studies with DMXBA (GTS-21). *Behav Brain Res* 113:169-181.

Kuryatov A, Onksen J and Lindstrom J (2008) Roles of accessory subunits in alpha4beta2(*) nicotinic receptors. *Mol Pharmacol* 74:132-143.

Lai I C, Hong C J and Tsai S J (2001) Association study of nicotinic-receptor variants and major depressive disorder. *J Affect Disord* 66:79-82.

Leonard S, Breese C, Adams C, Benhammou K, Gault J, Stevens K, Lee M, Adler L, Olincy A, Ross R and Freedman R (2000) Smoking and schizophrenia: abnormal nicotinic receptor expression. *Eur J Pharmacol* 393:237-242.

Leonard S, Mexal S and Freedman R (2007) Smoking, Genetics and Schizophrenia: Evidence for Self Medication. *J Dual Diagn* 3:43-59.

Lester H A, Xiao C, Srinivasan R, Son C D, Miwa J, Pantoja R, Banghart M R, Dougherty D A, Goate A M and Wang J C (2009) Nicotine is a selective pharmacological chaperone of acetylcholine receptor number and stoichiometry. Implications for drug discovery. *AAPS J* 11:167-177.

Lester R A (2004) Activation and desensitization of heteromeric neuronal nicotinic receptors: implications for nonsynaptic transmission. *Bioorg Med Chem Lett* 14:1897-1900.

Lopez-Hernandez G, Placzek A N, Thinschmidt J S, Lestage P, Trocme-Thibierge C, Morain P and Papke R L (2007) Partial agonist and neuromodulatory activity of S 24795 for alpha7 nAChR responses of hippocampal interneurons. *Neuropharmacology* 53:134-144.

Luetje C W and Patrick J (1991) Both α- and β-subunits contribute to the agonist sensitivity of neuronal nicotinic acetylcholine receptors. *J. Neurosci.* 11:837-845.

Mansvelder H D, Keath J R and McGehee D S (2002) Synaptic mechanisms underlie nicotine-induced excitability of brain reward areas. *Neuron* 33:905-919.

Marks M J, Meinerz N M, Brown R W and Collins A C 86Rb+ efflux mediated by alpha4beta2*-nicotinic acetylcholine receptors with high and low-sensitivity to stimulation by acetylcholine display similar agonist-induced desensitization. *Biochem Pharmacol* 80:1238-1251.

Martin L F and Freedman R (2007) Schizophrenia and the alpha7 nicotinic acetylcholine receptor. *Int Rev Neurobiol* 78:225-246.

McClure J B, Swan G E, Jack L, Catz S L, Zbikowski S M, McAfee T A, Deprey M, Richards J and Javitz H (2009) Mood, Side-effects and Smoking Outcomes Among Persons With and Without Probable Lifetime Depression Taking Varenicline. *J Gen Intern Med*.

Miller D K, Sumithran S P and Dwoskin L P (2002) Bupropion inhibits nicotine-evoked [(3)H]overflow from rat striatal slices preloaded with [(3)H]dopamine and from rat hippocampal slices preloaded with [(3)H]norepinephrine. *J Pharmacol Exp Ther* 302:1113-1122.

Mineur Y S, Eibl C, Young G, Kochevar C, Papke R L, Gundisch D and Picciotto M R (2009) Cytisine-based nicotinic partial agonists as novel antidepressant compounds. *J Pharmacol Exp Ther* 329:377-386.

Mineur Y S and Picciotto M R (2009) Biological basis for the co-morbidity between smoking and mood disorders. *J Dual Diagn* 5:122-130.

Nelson M E, Kuryatov A, Choi C H, Zhou Y and Lindstrom J (2003) Alternate stoichiometries of alpha4beta2 nicotinic acetylcholine receptors. *Mol Pharmacol* 63:332-341.

Olincy A, Harris J G, Johnson L L, Pender V, Kongs S, Allensworth D, Ellis J, Zerbe G O, Leonard S, Stevens K E, Stevens J O, Martin L, Adler L E, Soti F, Kern W R and Freedman R (2006) Proof-of-concept trial of an alpha7 nicotinic agonist in schizophrenia. *Arch Gen Psychiatry* 63:630-638.

Olincy A and Stevens KE (2007) Treating schizophrenia symptoms with an alpha7 nicotinic agonist, from mice to men. *Biochem Pharmacol* 74:1192-1201.

Papke R L (2009) Tricks of Perspective: Insights and limitations to the study of macroscopic currents for the analysis of nAChR activation and desensitization. *J. Mol. Neurosci.* 40:77-86.

Papke R L and Heinemann S F (1994) The partial agonist properties of cytisine on neuronal nicotinic receptors containing the beta2 subunit. *Mol. Pharm.* 45:142-149.

Papke R L, Kern W R, Soti F, LOpez-Hernandez G Y and Horenstein N A (2009) Activation and desensitization of nicotinic alpha7-type acetylcholine receptors by benzylidene anabaseines and nicotine. *J. P. E. T.* 329:791-807.

Papke R L, Meyer E, Nutter T and Uteshev V V (2000) Alpha7-selective agonists and modes of alpha7 receptor activation. *Eur J Pharmacol* 393:179-195.

Papke R L and Papke J K P (2002) Comparative pharmacology of rat and human alpha7 nAChR conducted with net charge analysis. *Br J of Pharm* 137:49-61.

Papke R L and Stokes C (2010) Working with OpusXpress: Methods for high volume oocyte experiments. *Methods*.

Picciotto M, Zoli M, Rimondini R, Lena C, Marubio L, Pich E, Fuxe K and Changeux J (1998) Acetylcholine receptors containing the beta2 subunit are involved in the reinforcing properties of nicotine. *Nature* 391:173-177.

Picciotto M R, Addy N A, Mineur Y S and Brunzell D H (2008) It is not "either/or": activation and desensitization of nicotinic acetylcholine receptors both contribute to behaviors related to nicotine addiction and mood. *Prog Neurobiol* 84: 329-342.

Pittenger C and Duman R S (2008) Stress, depression, and neuroplasticity: a convergence of mechanisms. *Neuropsychopharmacology* 33:88-109.

Saccone S F, Hinrichs A L, Saccone N L, Chase G A, Konvicka K, Madden P A, Breslau N, Johnson E O, Hatsukami D, Pomerleau O, Swan G E, Goate A M, Rutter J, Bertelsen S, Fox L, Fugman D, Martin N G, Montgomery G W, Wang J C, Ballinger D G, Rice J P and Bierut L J (2007) Cholinergic nicotinic receptor genes implicated in a nicotine dependence association study targeting 348 candidate genes with 3713 SNPs. *Hum Mol Genet.* 16:36-49.

Slemmer J E, Martin B R and Damaj M I (2000) Bupropion is a nicotinic antagonist. *J. Pharmacol. Exp. Ther.* 295:321-327.

Walsh H, Govind A P, Mastro R, Hoda J C, Bertrand D, Vallejo Y and Green W N (2008) Up-regulation of nicotinic receptors by nicotine varies with receptor subtype. *J Biol Chem* 283:6022-6032.

Zhou Y, Nelson M E, Kuryatov A, Choi C, Cooper J and Lindstrom J (2003) Human alpha4beta2 acetylcholine receptors formed from linked subunits. *J Neurosci* 23:9004-9015.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A method of reducing nicotine-induced rewarding effects in a subject who smokes comprising: delivering to a subject in need thereof a pharmaceutical composition, wherein the pharmaceutical composition includes a therapeutically effective amount of each of a α7 N-acetylcholine receptor (nAChR)-selective partial agonist and a α4β2 nAChR partial agonist, or a pharmaceutically acceptable salt of one or both of the α7-selective partial agonist and the α4β2 nAChR partial agonist, and a pharmaceutically acceptable carrier, wherein the α7 nAChR-selective partial agonist is 3-(2,4-dimethoxybenzylidene)anabaseine (DiMeOBA) (GTS-21) and in an amount therapeutically effective for reducing depression induced in said subject by the α4β2 nAChR partial agonist, and wherein the α4β2 nAChR partial agonist is varenicline, and in an amount therapeutically effective for reducing nicotine-induced rewarding effects in a subject by reducing the agonist effect of nicotine on the α4β2 nAChR.

2. A method of reducing nicotine-induced rewarding effects in a subject who smokes comprising: delivering to a subject in need thereof, a therapeutically effective amount of both a α7 N-acetylcholine receptor (nAChR)-selective partial agonist and a α4β2 nAChR partial agonist or a pharmaceutically acceptable salt of one or both of the α7 nAChR-selective partial agonist and the α4β2 nAChR partial agonist, wherein the α7 nAChR-selective partial agonist is 3-(2,4-dimethoxybenzylidene)anabaseine (DiMeOBA) (GTS-21),or a pharmaceutically acceptable salt thereof, and in an amount therapeutically effective for reducing depression induced in said subject by the α4β2 nAChR partial agonist, and wherein the α4β2 nAChR partial agonist is varenicline, or a pharmaceutically acceptable salt thereof, and in an amount therapeutically effective for reducing nicotine-induced rewarding effects in a subject by reducing the agonist effect of nicotine on the α4β2 nAChR.

3. The method of claim 2, wherein the α7 nAChR-selective partial agonist and the α4β2 nAChR partial agonist are separately delivered to the subject.

4. The method of claim 2, wherein the α7 nAChR-selective partial agonist and the α4β2 nAChR partial agonist are delivered to the subject in a composition including both the α7-selective partial agonist and the α4β2 nAChR partial agonist.

5. A method of reducing nicotine-induced rewarding effects in a subject who smokes comprising:
delivering to a subject in need thereof, a pharmaceutical composition comprising:
the α4β2 N-acetylcholine receptor (nAChR) partial agonist varenicline, or a pharmaceutically acceptable salt thereof, in an amount therapeutically effective for reducing nicotine-induced rewarding effects in a subject by reducing the agonist effect of nicotine on the α4β2 nAChR;
the α7 nAChR-selective partial agonist 3-(2,4-dimethoxybenzylidene)anabaseine (DiMeOBA) (GTS-21), or a pharmaceutically acceptable salt thereof, in an amount therapeutically effective for reducing depression induced in said subject by the α4β2 nAChR partial agonist; and
a pharmaceutically acceptable carrier.

6. A method of reducing nicotine-induced rewarding effects in a subject who smokes comprising:
delivering to a subject in need thereof:
the α4β2 nAChR partial agonist varenicline, or a pharmaceutically acceptable salt thereof, in an amount therapeutically effective for reducing the agonist effect of nicotine on the α4β2 nAChR;
the α7 nAChR-selective partial agonist 3-(2,4-dimethoxybenzylidene)anabaseine (DiMeOBA) (GTS-21), or a pharmaceutically acceptable salt thereof, in an amount therapeutically effective for reducing depression induced in said subject by the α4β2 nAChR partial agonist.

7. The method of claim 6, wherein the α7 nAChR-selective partial agonist and the α4β2 nAChR partial agonist are separately delivered to the subject.

8. The method of claim 6, wherein the α7 nAChR-selective partial agonist and the α4β2 partial agonist are delivered to the subject in a composition including both the α7 nAChR-selective partial agonist and the α4β2 nAChR partial agonist.

* * * * *